(12) United States Patent
Bechtel et al.

(10) Patent No.: US 12,733,827 B2
(45) Date of Patent: Sep. 15, 2026

(54) OPTICAL SENSOR MODULE

(71) Applicant: ROCKLEY PHOTONICS LIMITED, Altrincham (GB)

(72) Inventors: Kate LeeAnn Bechtel, Pleasant Hill, CA (US); James McMillan, Santa Monica, CA (US)

(73) Assignee: ROCKLEY PHOTONICS LIMITED, Altrincham (GB)

( * ) Notice: Subject to any disclaimer, the term of this patent is extended or adjusted under 35 U.S.C. 154(b) by 184 days.

(21) Appl. No.: 18/667,608

(22) Filed: May 17, 2024

(65) Prior Publication Data

US 2024/0298907 A1 Sep. 12, 2024

Related U.S. Application Data

(63) Continuation-in-part of application No. 17/934,502, filed on Sep. 22, 2022, now Pat. No. 12,193,800, (Continued)

(51) Int. Cl.
*A61B 5/024* (2006.01)
*A61B 5/00* (2006.01)

(52) U.S. Cl.
CPC ...... *A61B 5/02433* (2013.01); *A61B 5/02438* (2013.01); *A61B 5/681* (2013.01)

(58) Field of Classification Search
CPC . A61B 5/02433; A61B 5/02438; A61B 5/681; A61B 5/0295; A61B 5/02007;
(Continued)

(56) References Cited

U.S. PATENT DOCUMENTS 4,674,011 A 6/1987 Patton et al.
5,243,983 A 9/1993 Tarr et al.
(Continued)

FOREIGN PATENT DOCUMENTS

CA 2 861 089 C 1/2021
CN 108709847 A 10/2018
(Continued)

OTHER PUBLICATIONS

"NanEye Miniature Camera Module", ams Datasheet, Feb. 23, 2021, pp. 1-34, www.mouser.com.
(Continued)

*Primary Examiner* — Eugene T Wu
(74) *Attorney, Agent, or Firm* — Martin W. Regehr

(57) ABSTRACT

A wearable device includes a first optical sensor module, the first optical sensor module including: an image sensor configured to receive light from biological tissue; a photodiode configured to receive light from the tissue; a light source comprising a laser and being configured to illuminate, through the tissue, each of the image sensor and the photodiode, a distance between the image sensor and the photodiode being less than 50% of the distance between the image sensor and the light source; at least one processing circuit configured to process first data corresponding to a first light signal received by the image sensor from the light source to generate a speckleplethysmography (SPG) measurement, and to process second data corresponding to a second light signal received by the photodiode from the light source to generate a photoplethysmography (PPG) measurement.

20 Claims, 24 Drawing Sheets

Related U.S. Application Data which is a continuation of application No. 17/711, 974, filed on Apr. 1, 2022, now Pat. No. 12,390,117.

(60) Provisional application No. 63/279,932, filed on Nov. 16, 2021.

(58) Field of Classification Search
CPC .............. A61B 5/0205; A61B 5/02405; A61B 5/02416; A61B 5/02427; A61B 5/0261
See application file for complete search history.

(56) References Cited

U.S. PATENT DOCUMENTS 5,497,769 A 3/1996 Gratton et al.
5,532,860 A 7/1996 Hershey et al.
5,772,587 A 6/1998 Gratton et al.
5,830,132 A 11/1998 Robinson
6,154,259 A 11/2000 Hargis et al.
6,243,601 B1 6/2001 Wist
6,246,892 B1 6/2001 Chance
6,256,016 B1 7/2001 Piot et al.
6,560,478 B1 5/2003 Alfano et al.
6,919,549 B2 7/2005 Bamji et al.
7,035,679 B2 4/2006 Addison et al.
7,113,817 B1 9/2006 Winchester, Jr. et al.
7,202,466 B2 4/2007 Babayoff et al.
7,250,317 B2 7/2007 Heideman
7,295,783 B2 11/2007 Singh et al.
7,375,812 B2 5/2008 Atia et al.
7,474,407 B2 1/2009 Gutin
7,505,128 B2 3/2009 Zribi et al.
7,616,984 B2 11/2009 Barbour et al.
7,761,126 B2 7/2010 Gardner et al.
7,865,225 B2 1/2011 Kaltschmidt et al.
7,922,664 B2 4/2011 Elliott
7,925,056 B2 4/2011 Presura et al.
8,237,927 B1 8/2012 Reeve et al.
8,277,384 B2 10/2012 Fine
8,313,439 B2 11/2012 McCombie et al.
8,343,062 B2 1/2013 Fortin et al.
8,343,063 B2 1/2013 Borgos
8,376,955 B2 2/2013 Baker, Jr.
8,398,556 B2 3/2013 Sethi et al.
8,868,149 B2 10/2014 Eisen et al.
8,920,332 B2 12/2014 Hong et al.
8,923,942 B2 12/2014 Bernreuter
8,945,017 B2 2/2015 Venkatraman et al.
8,948,832 B2 2/2015 Hong et al.
8,956,303 B2 2/2015 Hong et al.
8,998,815 B2 4/2015 Venkatraman et al.
9,005,129 B2 4/2015 Venkatraman et al.
9,113,794 B2 8/2015 Hong et al.
9,113,795 B2 8/2015 Hong et al.
9,149,216 B1 10/2015 Eisen et al.
9,155,480 B2 10/2015 Thakor et al.
9,226,673 B2 1/2016 Ferguson, Jr. et al.
9,237,855 B2 1/2016 Hong et al.
9,307,917 B2 4/2016 Hong et al.
9,494,567 B2 11/2016 Islam
9,687,162 B2 6/2017 Vetter et al.
9,704,050 B2 7/2017 Lee et al.
9,730,622 B2 8/2017 Eisen et al.
9,772,280 B2 9/2017 Cerussi et al.
9,804,027 B2 10/2017 Fish et al.
9,846,126 B2 12/2017 Gunn, III et al.
9,848,787 B2 12/2017 White et al.
9,851,298 B1 12/2017 Isikman et al.
9,877,681 B2 1/2018 Silverman
9,931,040 B2 4/2018 Homyk et al.
9,970,955 B1 5/2018 Homyk et al.
10,004,406 B2 6/2018 Yuen et al.
10,058,256 B2 8/2018 Chen et al.
10,178,959 B1 1/2019 Homyk et al.
10,178,973 B2 1/2019 Venkatraman et al.
10,194,808 B1 2/2019 Thompson et al.
10,206,576 B2 2/2019 Shcherbakov et al.
10,215,698 B2 2/2019 Han et al.
10,241,033 B2 3/2019 Uematsu et al.
10,271,740 B2 4/2019 Ward et al.
10,314,532 B2 6/2019 Ward et al.
10,326,035 B2 6/2019 Lu et al.
10,326,036 B2 6/2019 Sweeney et al.
10,349,847 B2 7/2019 Kwon et al.
10,352,768 B2 7/2019 Simpkin et al.
10,357,165 B2 7/2019 Yoon
10,420,498 B1 9/2019 Horstmeyer et al.
10,422,693 B2 9/2019 Fish et al.
10,451,537 B2 10/2019 Nakaji
10,463,286 B2 11/2019 Schenkman et al.
10,492,684 B2 12/2019 Khachaturian et al.
10,506,926 B2 12/2019 Khachaturian et al.
10,506,955 B2 12/2019 Tholl et al.
10,568,527 B2 2/2020 Yoon et al.
10,588,519 B2 3/2020 Yuen et al.
10,602,987 B2 3/2020 Khachaturian et al.
10,627,849 B1 4/2020 Scofield et al.
10,641,962 B2 5/2020 Nykänen et al.
10,643,903 B2 5/2020 Drake et al.
10,667,688 B2 6/2020 Khachaturian et al.
10,677,989 B2 6/2020 Abediasl et al.
10,681,259 B2 6/2020 Ichiki et al.
10,681,283 B2 6/2020 Nakashima et al.
10,694,997 B2 6/2020 Kim et al.
10,718,668 B2 7/2020 Gu et al.
10,722,177 B2 7/2020 Homyk et al.
10,739,256 B1 8/2020 Rickman et al.
10,750,956 B2 8/2020 Zalevsky et al.
10,775,239 B2 9/2020 Lee et al.
10,813,597 B2 10/2020 Rice et al.
10,820,858 B2 11/2020 Yoon et al.
10,842,422 B2 11/2020 Yu et al.
10,871,503 B1 12/2020 Homyk et al.
10,895,525 B2 1/2021 Swanson
10,966,616 B2 4/2021 De Morree et al.
10,973,422 B2 4/2021 Pantelopoulos et al.
11,022,751 B2 6/2021 Bauters et al.
11,045,103 B2 6/2021 Shchekin et al.
11,079,364 B2 8/2021 Leger et al.
11,096,601 B2 8/2021 Hong et al.
11,096,608 B2 8/2021 Van Dorpe et al.
11,129,544 B2 9/2021 Zalevsky et al.
11,202,582 B2 12/2021 Verkruijsse et al.
11,213,217 B2 1/2022 Han et al.
11,278,220 B2 3/2022 Tucker et al.
11,298,035 B2 4/2022 Huijbregts et al.
11,369,275 B2 6/2022 Song et al.
11,445,922 B2 9/2022 Naima
11,553,851 B2 1/2023 Kim et al.
11,583,185 B2 2/2023 Homyk et al.
11,666,238 B2 6/2023 Rege et al.
11,666,277 B2 6/2023 Yoon et al.
11,684,281 B2 6/2023 Pantelopoulos et al.
11,690,513 B2 7/2023 Hu et al.
11,696,693 B2 7/2023 Wong
11,709,120 B2 7/2023 Rice et al.
11,744,491 B2 9/2023 Dunn et al.
11,751,811 B2 9/2023 Sun et al.
11,759,116 B2 9/2023 White et al.
11,759,121 B2 9/2023 Mccann et al.
11,771,343 B2 10/2023 Sacha
11,800,990 B2 10/2023 White et al.
11,857,301 B1 1/2024 Homyk et al.
11,883,134 B2 1/2024 Leabman
11,890,081 B2 2/2024 Jang
11,980,451 B2 5/2024 Albert
12,109,006 B2 10/2024 Dunn et al.
12,396,648 B1 8/2025 McMillan
2002/0068859 A1 6/2002 Knopp
2002/0195496 A1 12/2002 Tsikos et al.
2003/0052169 A1 3/2003 Tsikos et al.
2003/0137669 A1 7/2003 Rollins et al.
2005/0249509 A1 11/2005 Nagarajan et al.
2006/0124829 A1 6/2006 Song et al.
2006/0132790 A1 6/2006 Gutin

(56) References Cited

U.S. PATENT DOCUMENTS

2006/0204175 A1 9/2006 Laurent-Lund et al.
2006/0247514 A1 11/2006 Panasyuk et al.
2007/0051601 A1 3/2007 Wang et al.
2007/0057182 A1 3/2007 Feuerbaum
2007/0093702 A1 4/2007 Yu et al.
2008/0097172 A1 4/2008 Sawada et al.
2008/0154126 A1 6/2008 Culver et al.
2008/0204752 A1 8/2008 Dorvee et al.
2008/0220512 A1 9/2008 Koh et al.
2008/0316567 A1 12/2008 Grasser et al.
2009/0177094 A1 7/2009 Brown et al.
2009/0202251 A1 8/2009 Shibayama
2009/0209834 A1 8/2009 Fine
2009/0284748 A1 11/2009 Melman et al.
2010/0004741 A1 1/2010 Gupta et al.
2010/0046234 A1 2/2010 Abu-Ageel
2010/0056928 A1 3/2010 Zuzak et al.
2010/0226646 A1 9/2010 Chan et al.
2011/0054277 A1 3/2011 Pinter et al.
2011/0082355 A1 4/2011 Eisen et al.
2011/0087108 A1 4/2011 Onoe et al.
2011/0196244 A1 8/2011 Ribas Ripoll et al.
2012/0130215 A1 5/2012 Fine et al.
2012/0232402 A1 9/2012 MacFarlane et al.
2013/0131475 A1 5/2013 Eisen et al.
2013/0190630 A1 7/2013 Borgos
2013/0204112 A1 8/2013 White et al.
2013/0278631 A1 10/2013 Border et al.
2014/0094666 A1 4/2014 Fine
2014/0118695 A1 5/2014 Shimada et al.
2014/0120319 A1 5/2014 Joseph
2014/0200423 A1* 7/2014 Eisen .................. A61B 5/7278 600/340
2014/0313524 A1 10/2014 Banyay et al.
2014/0316286 A1 10/2014 Addison et al.
2014/0376001 A1 12/2014 Swanson
2015/0157224 A1 6/2015 Carmon et al.
2015/0196251 A1 7/2015 Outwater et al.
2015/0201854 A1 7/2015 Hong et al.
2015/0323311 A1 11/2015 Muijs et al.
2016/0058300 A1 3/2016 Yoon et al.
2016/0066790 A1 3/2016 Shcherbakov et al.
2016/0106327 A1 4/2016 Yoon et al.
2016/0157736 A1 6/2016 Huang et al.
2016/0161685 A1 6/2016 Xu et al.
2016/0183882 A1 6/2016 Henley et al.
2016/0195473 A1 7/2016 Fujiwara et al.
2016/0242647 A1 8/2016 Ishii et al.
2016/0266337 A1 9/2016 Feng
2016/0278676 A1 9/2016 Eisen et al.
2016/0282265 A1 9/2016 Su et al.
2016/0287107 A1 10/2016 Szabados et al.
2016/0360966 A1 12/2016 Ishii et al.
2017/0007138 A1 1/2017 Kim et al.
2017/0014037 A1 1/2017 Coppola et al.
2017/0065184 A1 3/2017 Barak
2017/0105618 A1 4/2017 Schmoll et al.
2017/0108439 A1 4/2017 Stievater et al.
2017/0138789 A1 5/2017 Ivanov
2017/0164878 A1 6/2017 Connor
2017/0188851 A1 7/2017 LeBoeuf et al.
2017/0231513 A1 8/2017 Presura et al.
2017/0315292 A1 11/2017 Mullen et al.
2018/0020962 A1 1/2018 Yu et al.
2018/0045566 A1 2/2018 Fish et al.
2018/0064399 A1 3/2018 Buettgen et al.
2018/0110423 A1 4/2018 Presura et al.
2018/0160913 A1 6/2018 Fine
2018/0168465 A1 6/2018 Yamada et al.
2018/0202927 A1 7/2018 Isikman et al.
2018/0228363 A1 8/2018 Frisken et al.
2018/0238794 A1 8/2018 Kangas et al.
2018/0263519 A1 9/2018 Gu
2018/0283950 A1 10/2018 Ge et al.
2018/0296168 A1 10/2018 Rice et al.
2019/0005351 A1 1/2019 Zhou et al.
2019/0041736 A1 2/2019 Grunnet-Jepsen et al.
2019/0046056 A1 2/2019 Khachaturian et al.
2019/0053721 A1 2/2019 Boas et al.
2019/0094009 A1 3/2019 Aizawa et al.
2019/0094564 A1 3/2019 Rivera et al.
2019/0167118 A1 6/2019 Vilenskii et al.
2019/0175030 A1 6/2019 Verkruijsse et al.
2019/0336006 A1 11/2019 Horstmeyer et al.
2019/0343442 A1 11/2019 Aung et al.
2019/0343456 A1 11/2019 Kahlert et al.
2019/0369650 A1 12/2019 Swanson et al.
2019/0387972 A1 12/2019 Hu et al.
2019/0391243 A1 12/2019 Nicolaescu
2019/0391702 A1 12/2019 Jo et al.
2020/0003619 A1 1/2020 Hu et al.
2020/0011995 A1 1/2020 Send et al.
2020/0069225 A1 3/2020 Vizbaras et al.
2020/0100705 A1 4/2020 Dellimore et al.
2020/0143534 A1 5/2020 Wright et al.
2020/0158548 A1 5/2020 Rice et al.
2020/0196874 A1 6/2020 Rozental et al.
2020/0214602 A1 7/2020 Narumi et al.
2020/0237272 A1 7/2020 Lin et al.
2020/0249492 A1 8/2020 Maes
2020/0323440 A1 10/2020 Vule et al.
2020/0359948 A1* 11/2020 Dunn ................ A61B 5/14551
2020/0397351 A1 12/2020 Miyata
2021/0000385 A1 1/2021 Warren et al.
2021/0022623 A1 1/2021 Rice et al.
2021/0028602 A1 1/2021 Cao et al.
2021/0161408 A1 6/2021 Wakita
2021/0186431 A1 6/2021 Jung et al.
2021/0267471 A1 9/2021 Bonomi et al.
2021/0321887 A1 10/2021 Fukazawa et al.
2021/0330202 A1 10/2021 Konecky
2021/0338083 A1 11/2021 Sie et al.
2021/0386310 A1 12/2021 Hong et al.
2021/0405518 A1 12/2021 Lablans
2022/0015649 A1 1/2022 Ikuta et al.
2022/0018762 A1 1/2022 Ekin et al.
2022/0019861 A1 1/2022 Durr et al.
2022/0039679 A1 2/2022 Califa et al.
2022/0061644 A1 3/2022 Fontaine et al.
2022/0104822 A1 4/2022 Shelton, IV et al.
2022/0117557 A1 4/2022 Hsu et al.
2022/0196557 A1 6/2022 Zheng et al.
2022/0211286 A1 7/2022 Tank et al.
2022/0265158 A1 8/2022 Tokura
2022/0370010 A1 11/2022 Zilkie et al.
2022/0413143 A1 12/2022 Parsa et al.
2023/0003938 A1 1/2023 Zilkie et al.
2023/0039055 A1 2/2023 Gardner et al.
2023/0048766 A1 2/2023 Frey
2023/0064006 A1 3/2023 Kim et al.
2023/0087295 A1 3/2023 Dunn et al.
2023/0148885 A1 5/2023 Bechtel et al.
2023/0148886 A1 5/2023 Bechtel et al.
2023/0164444 A1 5/2023 Yang
2023/0225643 A1 7/2023 Scofield et al.
2023/0277062 A1 9/2023 Dalvi et al.
2023/0277075 A1 9/2023 Pantelopoulos et al.
2023/0296510 A1 9/2023 Xu
2023/0320598 A1 10/2023 Khine et al.
2023/0347029 A1 11/2023 Corso et al.
2023/0375525 A1 11/2023 Merritt et al.
2023/0397818 A1 12/2023 Newhouse et al.
2023/0401747 A1 12/2023 Dunn et al.
2024/0032790 A1 2/2024 Patel et al.
2024/0041342 A1 2/2024 Lai et al.
2024/0074667 A1 3/2024 Rick et al.
2024/0108289 A1 4/2024 Bechtel et al.
2024/0115212 A1 4/2024 Jang
2024/0156355 A1 5/2024 O'Brien et al.
2024/0350019 A1 10/2024 Pery-Shechter et al.
2024/0364420 A1 10/2024 Vallius et al.

(56) References Cited

U.S. PATENT DOCUMENTS

| | | | |
|---|---|---|---|
| 2025/0025058 A1 | 1/2025 | Bechtel et al. |
| 2025/0169696 A1 | 5/2025 | Dunn et al. |

FOREIGN PATENT DOCUMENTS

| | | | |
|---|---|---|---|
| CN | 110301896 B | 10/2019 |
| CN | 211094079 U | 7/2020 |
| CN | 211131004 U | 7/2020 |
| CN | 112639582 A | 4/2021 |
| CN | 114466549 A | 5/2022 |
| EP | 3 002 568 A1 | 4/2016 |
| EP | 2 395 958 B1 | 12/2017 |
| EP | 3 384 841 A1 | 10/2018 |
| EP | 3 558 119 B1 | 11/2020 |
| EP | 3 886 686 A0 | 10/2021 |
| EP | 3 903 676 A1 | 11/2021 |
| WO | WO 2018/029123 A1 | 2/2018 |
| WO | WO 2019/149815 A1 | 8/2019 |
| WO | WO 2019/233903 A1 | 12/2019 |
| WO | WO 2020/030641 A1 | 2/2020 |
| WO | WO 2020/114989 A1 | 6/2020 |
| WO | WO 2021/058338 A1 | 4/2021 |
| WO | WO 2021/094473 A1 | 5/2021 |
| WO | WO 2021/116766 A1 | 6/2021 |
| WO | WO 2021/116766 A8 | 6/2021 |
| WO | WO 2023/031927 A1 | 3/2023 |
| WO | WO 2023/245149 A2 | 12/2023 |
| WO | WO 2024/052289 A1 | 3/2024 |
| WO | WO 2024/173585 A1 | 8/2024 |

OTHER PUBLICATIONS

Abookasis, D. et al., "Feasibility study of hidden flow imaging based on laser speckle technique using multiperspectives contrast images", Optics and Lasers in Engineering, 2014, pp. 38-45.
Apsel, S. et al., "Rolling-Shutter Laser Speckle Analysis in Bio-Photonics", Proc. of SPIE, Jun. 20, 2024, pp. 130060U-1-130060U-4, vol. 13006, SPIE.
Bi, R. et al., "Fast pulsatile blood flow measurement in deep tissue through a multimode detection fiber", Journal of Biomedical Optics, May 13, 2020, pp. 055003-1 through 055003-10, vol. 25(5), SPIE.
Chen, Hsiang-Lin et al., "A CMOS Imager for Reflective Pulse Oximeter with Motion Artifact and Ambient Interference Rejections", 2018 IEEE Asian Solid-State Circuits Conference, Nov. 5-7, 2018, Taiwan, pp. 25-26, IEEE.
European Patent Office Communication pursuant to Article 94(3) EPC, for Patent Application No. 22776935.3, dated Jun. 24, 2025, 7 pages.
European Patent Office Communication pursuant to Rule 114(2) EPC, for Patent Application No. 22776935.3, mailed Aug. 9, 2024, 6 pages.
Goodman, J. W., "Some fundamental properties of speckle", Journal of the Optical Society of America, Nov. 1976, pp. 1145-1150, vol. 66, No. 11, Optical Society of America.
International Search Report and Written Opinion of the International Searching Authority, Mailed Dec. 11, 2024, Corresponding to PCT/IB2024/000388, 14 pages.
International Search Report and Written Opinion of the International Searching Authority, mailed Jan. 2, 2023, corresponding to PCT/EP2022/074876, 13 pages.
International Search Report and Written Opinion of the International Searching Authority, mailed Jun. 23, 2025, corresponding to PCT/IB2025/000070, 15 pages.
International Search Report and Written Opinion of the International Searching Authority, mailed May 14, 2025, corresponding to PCT/IB2025/000071, 15 pages.
Invitation to Pay Additional Fees and Partial International Search of the International Searching Authority, mailed Aug. 14, 2025, corresponding to PCT/IB2025/000235, 16 pages.
International Search Report and Written Opinion of the International Searching Authority, mailed Oct. 7, 2025, corresponding to PCT/IB2025/000235, 18 pages.
Mosso, E. et al., "Cluster speckle structures through multiple apertures forming a closed curve", Optics Communications, 2010, pp. 1285-1290, Elsevier B.V.
Nabeel, P. M. et al., "Local Pulse Wave Velocity: Theory, Methods, Advancements, and Clinical Applications", IEEE Reviews in Biomedical Engineering, Jul. 29, 2019, pp. 74-112, vol. 13, IEEE.
Qiu, J. et al., "Correcting speckle contrast at small speckle size to enhance signal to noise ratio for laser speckle contrast imaging", Optics Express, Nov. 15, 2013, pp. 28902-28913, vol. 21, No. 23, Optical Society of America.
Sdobnov, A. Y. et al. "Speckle dynamics under ergodicity breaking", Journal of Physics D: Applied Physics, Mar. 26, 2018, pp. 1-21, vol. 51, No. 15, IOP Publishing Ltd.
Teng, Zhongshuai et al., "In Vivo Pulse Wave Measurement Through a Multimode Fiber Diffuse Speckle Analysis System", Frontiers in Physics, Jan. 19, 2021, pp. 1-8, vol. 8, Article 613342, www.frontiersin.org.
U.S. Advisory Action for U.S. Appl. No. 17/822,419, dated May 2, 2024, 5 pages.
U.S. Advisory Action for U.S. Appl. No. 17/822,419, dated Oct. 10, 2023, 6 pages.
U.S. Appl. No. 18/991,054, filed Dec. 20, 2024.
U.S. Appl. No. 19/275,916, filed Jul. 21, 2025.
U.S. Appl. No. 19/390,480, filed Nov. 14, 2025.
U.S. Notice of Allowance for U.S. Appl. No. 17/703,920, dated Jul. 31, 2024, 10 pages.
U.S. Notice of Allowance from U.S. Appl. No. 17/822,419, dated Nov. 6, 2024, 10 pages.
U.S. Office Action for U.S. Appl. No. 17/703,920, dated Apr. 5, 2024, 11 pages.
U.S. Office Action for U.S. Appl. No. 17/822,419, dated Feb. 20, 2024, 12 pages.
U.S. Office Action for U.S. Appl. No. 17/822,419, dated Jun. 12, 2024, 12 pages.
U.S. Office Action for U.S. Appl. No. 17/822,419, dated Nov. 3, 2023, 18 pages.
U.S. Office Action from U.S. Appl. No. 17/822,419, dated Jul. 20, 2023, 21 pages.
U.S. Office Action from U.S. Appl. No. 17/822,419, dated Mar. 10, 2023, 17 pages.
U.S. Office Action from U.S. Appl. No. 18/778,893, dated Apr. 22, 2025, 9 pages.
U.S. Office Action from U.S. Appl. No. 18/778,893, dated Aug. 26, 2025, 8 pages.
U.S. Office Action from U.S. Appl. No. 18/984,845, dated Mar. 3, 2025, 7 pages.
U.S. Office Action from U.S. Appl. No. 18/991,054, dated Jun. 24, 2025, 23 pages.
U.S. Office Action from U.S. Appl. No. 18/991,054, dated Mar. 3, 2025, 19 pages.
Website: "0.07mm Dia., TO-46 Package, InGaAs Photodiode", 2022, printed Dec. 7, 2022, 1 page, Edmund Optics Inc., https://www.edmundoptics.com/p/ingaas-detector-70mum-dia-to-46/12571/.
Website: "FlowMet Peripheral Blood Flow Monitoring System", updated Oct. 2022, printed Dec. 7, 2022, 7 pages, https://www.medtronic.com/us-en/healthcare-professionals/products/cardiovascular/intraprocedural-monitoring/flowmet.html.
Xu, J. et al., "Interferometric speckle visibility spectroscopy (ISVS) for human cerebral blood flow monitoring", APL Photonics, Dec. 4, 2020, pp. 126102-1 through 126102-10, vol. 5. AIP Publishing.
Zalevsky, Z. et al., "Novel Approaches for Near and Far Field Super Resolved Imaging", 22nd Congress of the International Commision for Optics: Light for the Development of the World, Proc. of SPIE, Sep. 15, 2011, pp. 80116M-1 through 80116M-11, vol. 8011, No. 1, SPIE.
U.S. Office Action from U.S. Appl. No. 17/711,974, dated Oct. 11, 2024, 18 pages.
U.S. Office Action from U.S. Appl. No. 17/934,502, dated Jun. 5, 2024, 7 pages.

(56) References Cited

OTHER PUBLICATIONS

Akram, M. N. et al., "Laser speckle reduction due to spatial and angular diversity introduced by fast scanning micromirror", Applied Optics, Jun. 4, 2010, pp. 3297-3304, vol. 49, No. 17, Optical Society of America.
Baek, H. J. et al., "The Effect of Optical Crosstalk on Accuracy of Reflectance-Type Pulse Oximeter for Mobile Healthcare", Journal of Healthcare Engineering, Oct. 21, 2018, 9 pages, vol. 2018, Article ID 3521738, Hindawi, https://doi.org/10.1155/2018/3521738.
Baets, R. et al., "Spectroscopy-on-chip applications of silicon photonics", Proc. of SPIE, 2013, pp. 862701-1 through 862701-10, vol. 8627, SPIE.
Berger, A. J. et al., "Feasibility of measuring blood glucose concentration by near-infrared Raman spectroscopy", Spectrochimica Acta Part A, 1997, pp. 287-292, Elsevier Science B.V.
Bi, R. et al., "A speckle-based method for fast blood flow measurement in deep tissue", Proceedings of SPIE, Optical Biopsy XIX: Toward Real-Time Spectroscopic Imaging and Diagnosis, Mar. 5, 2021, pp. 1163606-1 through 1163606-5, vol. 11636, SPIE.
Biswas, A. et al., "Fast diffuse correlation spectroscopy with a low-cost, fiber-less embedded diode laser", Biomedical Optics Express, Oct. 4, 2021, pp. 6686-6700, vol. 12, No. 11, Optical Society of America.
Brouckaert, J. et al., "Silicon-on-Insulator Microspectrometer", Proceedings Symposium IEEE/LEOS Benelux Chapter, 2008, pp. 7-10, IEEE.
Cole, D. B. et al., "Integrated heterodyne interferometer with on-chip modulators and detectors", Optics Letters, Jun. 25, 2015, pp. 3097-3100, vol. 40, No. 13, Optical Society of America.
Epping, J. P. et al., "High power, tunable, narrow linewidth dual gain hybrid laser", Laser Congress, Oct. 3, 2019, pp. 1-2.
Fu, D. et al., "In Vivo Metabolic Fingerprinting of Neutral Lipids with Hyperspectral Stimulated Raman Scattering Microscopy", Journal of the American Chemical Society, May 28, 2014, pp. 8820-8828, American Chemical Society Publications.
Fukui, T. et al., "Single-Pixel Imaging Using Multimode Fiber and Silicon Photonic Phased Array", Journal of Lightwave Technology, Jul. 14, 2020, pp. 839-844, vol. 39, No. 3, IEEE.
Ge, Z. et al., "Dynamic laser speckle analysis using the event sensor", Applied Optics, Dec. 23, 2020, pp. 172-178, vol. 60, No. 1, Optical Society of America.
Ghijsen, M. et al., "Wearable speckle plethysmography (SPG) for characterizing microvascular flow and resistance", Biomedical Optics Express, Jul. 30, 2018, pp. 3937-3952, vol. 9, No. 8, Optical Society of America under the terms of the OSA Open Access Publishing Agreement.
Gottschling, K. et al., "Molecular Insights into Carbon Dioxide Sorption in Hydrazone-Based Covalent Organic Frameworks with Tertiary Amine Moieties", Chemistry of Materials, Feb. 13, 2019, pp. 1946-1955, American Chemical Society.
Hashimoto, Y. et al., "Fabrication of an Anti-Reflective and Super-Hydrophobic Structure by Vacuum Ultraviolet Light-Assisted Bonding and Nanoscale Pattern Transfer", Micromachines, Apr. 15, 2018, pp. 1-11, www.mdpi.com/journal/micromachines.
Hollis, V. S. et al., "Non-invasive monitoring of brain tissue temperature by near-infrared spectroscopy", Proceedings of SPIE, Optical Tomography and Spectroscopy of Tissue IV, Jun. 29, 2001, pp. 470-481, vol. 4250, SPIE, https://www.spiedigitallibrary.org/conference-proceedings-of-spie/4250/1/Noninvasive-monitoring-of-brain-tissue-temperature-by-near-infrared-spectroscopy/10.1117/12.434506.short?SSO=1.
International Search Report and Written Opinion of the International Searching Authority, Mailed Mar. 11, 2021, Corresponding to PCT/IB2020/001037, 13 pages.
International Search Report and Written Opinion of the International Searching Authority, mailed Apr. 4, 2023, corresponding to PCT/EP2022/082341, 33 pages.
International Search Report and Written Opinion of the International Searching Authority, mailed Feb. 1, 2022, corresponding to PCT/IB2021/000649, 18 pages.
International Search Report and Written Opinion of the International Searching Authority, mailed Nov. 15, 2021, corresponding to PCT/IB2021/000517, 15 pages.
International Search Report and Written Opinion of the International Searching Authority, mailed Oct. 10, 2022, corresponding to PCT/IB2022/000373, 16 pages.
International Search Report and Written Opinion of the International Searching Authority, mailed Oct. 19, 2022, corresponding to PCT/EP2022/071467, 16 pages.
International Search Report and Written Opinion of the International Searching Authority, mailed Feb. 14, 2023, corresponding to PCT/EP2022/082162, 33 pages.
Invitation to Pay Additional Fees and Partial Search Report mailed Feb. 14, 2023 in related International Application No. PCT/EP2022/082341, 18 pages.
Izutsu, M. et al., "Integrated Optical SSB Modulator/Frequency Shifter", IEEE Journal of Quantum Electronics, Nov. 1981, pp. 2225-2227, vol. QE-17, No. 11, IEEE.
Kang, J. W. et al., "Direct observation of glucose fingerprint using in vivo Raman spectroscopy," Science Advances, Jan. 24, 2020, pp. 1-8, American Association for the Advancement of Science.
Karlsson, C. J. et al., "All-fiber multifunction continuous-wave coherent laser radar at 1.55 um for range, speed, vibration, and wind measurements", Applied Optics, Jul. 20, 2000, pp. 3716-3726, vol. 39, No. 21, Optical Society of America.
Lai, M. et al., "Perfusion Monitoring by Contactless Photoplethysmography Imaging", 2019 IEEE 16th International Symposium on Biomedical Imaging (ISBI 2019), Venice, Italy, Apr. 8-11, 2019, pp. 1778-1782, IEEE.
Lai, N. et al., "CO2 Capture With Absorbents of Tertiary Amine Functionalized Nano-SiO2", Frontiers in Chemistry, Feb. 28, 2020, pp. 1-9, vol. 8, Article 146, www.frontiersin.org.
Lapchuk, A. et al., "Investigation of speckle suppression beyond human eye sensitivity by using a passive multimode fiber and a multimode fiber bundle", Applied Optics, Feb. 21, 2020, pp. 6820-6834, vol. 28, No. 5, Optical Society of America.
Liu, X. et al., "Simultaneous measurements of tissue blood flow and oxygenation using a wearable fiber-free optical sensor", Journal of Biomedical Optics, Jan. 29, 2021, pp. 012705-1 through 012705-15, vol. 26, No. 1, SPIE.
Loi, R. et al., "Transfer Printing of AlGaInAs/InP Etched Facet Lasers to Si Substrates", IEEE Photonics Journal, Nov. 11, 2016, 11 pages, vol. 8, No. 6, IEEE.
Lu, H. et al., "Single-trial estimation of the cerebral metabolic rate of oxygen with imaging photoplethysmography and laser speckle contrast imaging", Optics Letters, Mar. 17, 2015, pp. 1193-1196, vol. 40, No. 7, Optical Society of America.
Mehta, D. S. et al., "Laser speckle reduction by multimode optical fiber bundle with combined temporal, spatial, and angular diversity", Applied Optics, Apr. 11, 2012, pp. 1894-1904, vol. 51, No. 12, Optical Society of America.
Merritt, S. et al., "Monitoring temperature non-invasively using broadband Diffuse Optical Spectroscopy", OSA/FIO, 2004, 1 page, Optical Society of America, https://opg.optica.org/abstract.cfm?URI=FiO-2004-FTuK4.
Noriki, A. et al., "45-degree curved micro-mirror for vertical optical I/O of silicon photonics chip", Optics Express, Jul. 1, 2019, pp. 19749-19757, vol. 27, No. 14, Optical Society of America, https://doi.org/10.1364/OE.27.019749.
Poulton, C. V. et al., "Frequency-modulated Continuous-wave LIDAR Module in Silicon Photonics", OFC, 2015, 4 pages, Optical Society of America.
Redding, B. et al., "Compact spectrometer based on a disordered photonic chip", Nature Photonics, Jul. 28, 2013, pp. 746-751, vol. 7, Macmillan Publishers Limited.
Redding, B. et al., "Evanescently coupled multimode spiral spectrometer", Optica, Aug. 25, 2016, pp. 956-962, vol. 3, No. 9, Optical Society of America.
Robinson, M. B., "Interferometric diffuse correlation spectroscopy improves measurements at long source-detector separation and low

(56) References Cited

OTHER PUBLICATIONS photon count rate", Journal of Biomedical Optics, Sep. 30, 2020, pp. 097004-1 through 097004-12, vol. 25, No. 9, SPIE.
Roelkens, G. et al., "Transfer printing for silicon photonics transceivers and interposers" 2018 IEEE Optical Interconnects Conference, Jun. 4, 2018, pp. 13-14, IEEE.
Ryckeboer, E., "Spectroscopic Detection of Glucose with a Silicon Photonic Integrated Circuit", Universiteit Gent, Jan. 1, 2014, 263 pages, ISBN 978-90-8578-688-7, http://www.photonics.intec.ugent.be/download/phd_206.pdf.
Schneider, S. et al., "Optical coherence tomography system mass-producible on a silicon photonic chip", Optics Express, Jan. 20, 2016, pp. 1573-1586, vol. 24, No. 2, Optical Society of America.
Shimotsu, S. et al., "Single Side-Band Modulation Performance of a LiNbO3 Integrated Modulator Consisting of Four-Phase Modulator Waveguides", IEEE Photonics Technology Letters, Apr. 2001, pp. 364-366, vol. 13, No. 4, IEEE.
Subramanian, A. Z. et al., "Silicon and silicon nitride photonic circuits for spectroscopic sensing on-a-chip [Invited]", Photon. Res., Aug. 28, 2015, pp. B47-B59, vol. 3, No. 5, Chinese Laser Press.
Timm, U. et al., "Non-Invasive Optical Real-time Measurement of Total Hemoglobin Content", Procedia Engineering, 2010, pp. 488-491, Elsevier Ltd.
Tran, T-T-K. et al., "Speckle reduction in laser projection displays through angle and wavelength diversity", Applied Optics, Feb. 16, 2016, pp. 1267-1274, vol. 55, No. 6, Optical Society of America.
Tuchin, V., "Chapter 8: Coherent Effects at the Interaction of Laser Radiation with Tissues and Cell Flows", Tissue Optics Light Scattering Methods and Instruments for Medical Diagnostics, 3rd Edition, 2015, pp. 359-417, SPIE.
U.S. Notice of Allowance from U.S. Appl. No. 17/757,130, dated Jan. 18, 2023, 10 pages.
U.S. Office Action from U.S. Appl. No. 17/934,502, dated Aug. 31, 2023, 6 pages.
U.S. Office Action from U.S. Appl. No. 17/934,502, dated Feb. 1, 2024, 6 pages.
Valley, G.C. et al., "Multimode waveguide speckle patterns for compressive sensing", Optics Letters, May 23, 2016, pp. 2529-2532, vol. 41, No. 11, Optical Society of America.
Van Gastel, M. et al., "Camera-based pulse-oximetry—validated risks and opportunities from theoretical analysis", Biomedical Optics Express, Dec. 5, 2017, pp. 102-119, vol. 9, No. 1, Optical Society of America.
Website: "Optical Solutions", Molex, dated 2023, printed May 10, 2023, 13 pages, Molex, LLC, https://www.molex.com/en-us/products/optical-solutions.
Website: "Track Your SpO2 to Uncover Changes in Your Wellbeing", Fitbit News, dated Sep. 7, 2020, printed Apr. 17, 2023, 7 pages, Fitbit, Inc., https://blog.fitbit.com/track-your-spo2/).626.
Wenz, J. J., "Examining water in model membranes by near infrared spectroscopy and multivariate analysis", BBA—Biomembranes, Dec. 9, 2017, pp. 673-682, Elsevier B.V., https://www.sciencedirect.com/science/article/pii/S0005273617303905.
Xu, M. et al., "Laser Speckle Reduction Using a Motionless Despeckle Element Based on Random Mie Scattering", Journal of Display Technology, Nov. 12, 2013, pp. 151-156, vol. 10, No. 2, IEEE.
Yamakoshi, Y. et al., "Side-scattered finger-photoplethysmography: experimental investigations toward practical noninvasive measurement of blood glucose", Journal of Biomedical Optics, Jun. 2017, pp. 067001-1 through 067001-11, vol. 22, No. 6, SPIE.
Yao, Z. et al., "Integrated Silicon Photonic Microresonators: Emerging Technologies", IEEE Journal of Selected Topics in Quantum Electronics, Jun. 11, 2018, 24 pages, vol. 24, No. 6, IEEE.
Zhang, J. et al., "III-V-on-Si photonic integrated circuits realized using micro-transfer-printing", APL Photonics, Nov. 4, 2019, pp. 110803-1 through 110803-10.
Zijlstra, W. G. et al., "Absorption Spectra of Human Fetal and Adult Oxyhemoglobin, De-Oxyhemoglobin, Carboxyhemoglobin, and Methemoglobin", Clinical Chemistry, Sep. 1991, pp. 1633-1638, vol. 37, No. 9, https://academic.oup.com/clinchem/article-abstract/37/9/1633/5649610?redirectedFrom=fulltext.
Zilkie, A. J. et al., "Multi-Micron Silicon Photonics Platform for Highly Manufacturable and Versitile Photonic Integrated Circuits", IEEE Journal of Selected Topics in Quantum Electronics, Apr. 15, 2019, 13 pages, vol. 25, No. 5, IEEE.
Zilkie, A. J. et al., "Power-efficient III-V/Silicon external cavity DBR lasers", Optics Express, Sep. 27, 2012, pp. 23456-23462, vol. 20, No. 21, Optical Society of America.

* cited by examiner

OPTICAL SENSOR MODULE

CROSS-REFERENCE TO RELATED APPLICATIONS

The present application is a continuation-in-part of U.S. patent application Ser. No. 17/934,502, filed Sep. 22, 2022, entitled "OPTICAL SENSOR MODULE", which is a continuation of U.S. patent application Ser. No. 17/711,974, filed Apr. 1, 2022, entitled "OPTICAL SENSOR MODULE", which claims priority to and the benefit of U.S. Provisional Application No. 63/279,932, filed Nov. 16, 2021, entitled "COMBINED OPTICAL SENSOR MODULE", the entire contents of all documents identified in this paragraph are hereby incorporated herein by reference as if fully set forth herein.

FIELD

Embodiments of the present invention relate to an optical sensor, particularly to an optical sensor module for measuring both speckleplethysmography (SPG) and photoplethysmography (PPG) signals at human tissue.

BACKGROUND

Photoplethysmography (PPG) signals are currently utilized to extract cardiovascular parameters such as heart rate (HR), pulsatile oxygen saturation (SpO2) and blood pressure (BP). PPG signals arise from the change in tissue absorption caused by blood volume variation during pulsatile flow. These AC signals are generally of low magnitude as compared to a DC background. This is especially true on the wrist, where the pulsatile signal may be on the order of 0.4% or less than the measured intensity at red wavelengths. Red and near infra-red (NIR) light sources are required to obtain SpO2 values. Most wearables that provide SpO2 at wrist do so only during a person's quiescent periods, such as at night, where many pulses can be averaged in order to overcome low signal quality. To obtain daily beat-to-beat heartbeat values, many PPG modules include a green LED that has higher responsivity to changes in blood absorption. However, the green light does not penetrate very deeply and the signal quality is impacted by pressure that reduces circulation in the microvasculature. It is also undesirable for many people to observe a bright green light in a wearable device during the night.

Furthermore, it is possible that blood pressure may be extracted with more accuracy and reliability from blood flow data (speckleplethysmography, SPG) or a combination of blood flow and PPG than from PPG signals alone. For this reason, it is advantageous to simultaneously collect both SPG and PPG signals for the purposes of obtaining HR, HRV, SpO2, and BP measurements. To obtain SpO2, either or both of SPG and PPG may be collected from at least two wavelengths. For co-oximetry measurements in which more than one form of modified hemoglobin is measured, such as methemoglobin and carboxyhemoglobin, many more than 2 wavelengths may be utilized, often 6 or more.

It may be desirable to obtain a host of cardiovascular parameters from one compact, body-worn module. This may be achieved through the combination of SPG and PPG signals. Previously, researchers have demonstrated a combined system for measuring blood flow and tissue oxygenation by utilizing two laser diodes (red, NIR/IR) and a CMOS image sensor [Liu et al. J. Biomed. Opt. 26(1) 012705-1, 2021]. The calculation of SPG via spatial contrast measurements involves measuring both the standard deviation and intensity of the speckle image and calculating the ratio. Therefore, the calculation uses a PPG signal, which is directly related to the measured image intensity. However, this method is not optimal for resolving the pulsatile PPG signal at medium to low blood volumes, such as would be the case for a consumer wearable device. Indeed, the authors only demonstrated tissue oxygen saturation, StO2, which is not the resolved pulsatile SpO2 signal.

Systems that are optimized for PPG measurements in consumer wearables include DC and ambient light subtraction prior to amplifying the AC signal in order to improve dynamic range and sensitivity. Additionally, the photodiodes used are generally large format (e.g. 2×3 mm) to increase the number of detected photons. Finally, it is typical to use LEDs which, unlike lasers, do not produce speckle noise in intensity measurements.

SUMMARY

Accordingly, embodiments of the present invention aim to solve the above problems by providing, according to one or more embodiments of a first aspect, an optical sensor module for measuring both speckleplethysmography (SPG) and photoplethysmography (PPG) signals at human tissue, the optical sensor module comprising: a first light source, for illuminating the human tissue for use with SPG measurements, the first light source comprising a laser; a second light source, for illuminating the human tissue for use with PPG measurements; and one or more optical sensor(s) for receiving light from the illuminated human tissue.

Herein, when it is stated that the optical sensor module is for measuring SPG and PPG signals "at human tissue", it should be understood that the light from the first and second laser sources is incident on the human tissue, and that the one or more optical sensors are configured to receive, and measure, light which is reflected and/or scattered from the surface of the human tissue, or from components of the tissue beneath the surface, and which is transmitted back through the tissue in a reflectance measurement geometry, or light that is only transmitted through the tissue in a transmission measurement geometry. In some cases, the one or more optical sensors may be arranged, in use, to be in contact with a user's skin, in which case the light from the first light source and the second light source may enter the user's tissue through the skin, and be reflected or scattered from components of the tissue beneath the skin, and then travel back through the tissue, whereupon, on being transmitted back through the skin, it may be detected by the one or more optical sensors. In alternative cases, the one or more optical sensors may be configured to be spaced from the user's skin in use, in which case the received light may further include light which is reflected from the surface of the user's skin.

In other cases, the one or more optical sensors may be configured to receive light which has been transmitted through the tissue. In those cases, the one or more optical sensors may still be arranged, in use, either to be in contact with the user's skin or spaced from the user's skin. Transmission may, for example, be transmission from one side of a finger, car, or toe to the other.

Some embodiments of the invention relate to illumination of organic tissue. This may be "human tissue" or "animal tissue". Herein, "human tissue" or "animal tissue" may refer to blood (e.g. blood cells or components thereof, such as the cell membranes), and elements of the vasculature (e.g. arteries, veins, capillaries, or walls thereof). It will be appreciated that different physiological parameters may be measured or otherwise determined based on illumination of different types of human tissue—this is discussed later in the application.

Optional features of the invention will now be set out. These are applicable singly or in any combination with any aspect of the invention.

Optionally, the first light source is a laser with a wavelength of operation lying within a red wavelength, which may be thought of as the range of 600 nm to 1000 nm, or the range from 620 nm to 1000 nm.

Optionally, the wavelength of operation of the laser is 660 nm or 760 nm.

Optionally, the second light source is an LED.

Optionally, the second light source is an LED operating at infra-red (IR) wavelengths (e.g. >800 nm).

Optionally, the second light source is an LED operating at a red wavelength, e.g. a wavelength within the range of 620 nm to 1000 nm.

Optionally, the first and second light sources are both lasers and are located on the same photonic integrated circuit (PIC).

Optionally, the first light source is a laser having a first wavelength, the second light source is an LED operating at a second wavelength, the optical sensor further comprising a third light source, the third light source comprising an LED operating at the first wavelength or a similar wavelength to the first wavelength.

Optionally, the first light source is a laser having a red wavelength within the range of 620 to 800 nm, the second light source is an LED operating at an IR wavelength within the range of 800 to 1000 nm, the optical sensor further comprising a third light source, the third light source comprising an LED operating at red wavelength within the range of 620 to 800 nm.

Optionally, the first and second light sources and the one or more optical sensor(s) are configured to carry out SPG and PPG measurements simultaneously or near-simultaneously.

Optionally, the one or more optical sensor(s) comprises an image sensor.

Optionally, the same image sensor is used to extract measurements from both the first light source and the second light source.

Optionally, the one or more optical sensor(s) is configured to carry out one or more of the following: in-pixel ambient/DC subtraction; near pixel ambient DC subtraction; pixel block statistics calculation; and/or pixel array statistics calculation.

Optionally, the one or more optical sensor(s) includes a processor configured to process captured data in-device and generate PPG and/or SPG output data.

Optionally, the one or more optical sensor(s) comprises an event-based image sensor.

Optionally, the one or more optical sensor(s) comprises a photodiode and separate sensor (e.g. CMOS).

Optionally, the optical sensor module further comprises one or more processors configured to convert optical measurement(s) at the one or more optical sensor(s) to measurements of one or more of the following: blood pressure, SpO2, arterial stiffness, heart rate, heart rate variability, atrial fibrillation, bradycardia, tachycardia, and/or movement such as steps taken or gestures.

Optionally, the optical sensor module may be located or locatable on a consumer wearable, typically understood to have a small form factor.

Optionally, the optical sensor may be located on or as part of a module. The module may be part of a strap or attached to a strap such that measurements are taken over the radial or ulnar arteries of the wrist.

Optionally, the optical sensor module may be located on a wrist strap of a wearable device.

Optionally, when the wearable device is located on the wrist of a user, one or more of the optical sensor(s) are located over the radial artery of the user.

Optionally, the wearable device includes a timepiece, and a strap that connects to the timepiece, and the entire optical sensor module is located on the strap. In this way, the smart strap may advantageously be used in combination with analogue timepieces. That is to say, the operation of the smart strap can be completely separate from the operation of the timepiece. This may be advantageous since there is limited space on the back of the wrist combined with user tolerance for stack height.

In addition, there remains a strong desire for analog timepieces, often in the higher price point market. Consumers must forgo health-related benefits to enjoy such timepieces, or wear two watches; a smartwatch that provides wellness/cardiovascular metrics and a quality analog timepiece.

Some embodiments of the present invention also provide for physiological benefits over prior art devices which may incorporate optical sensor(s) onto the timepiece itself to be located at the back of the wrist. The back of the wrist is actually not the ideal place from which to acquire biophotonic measurements owing to low vascularization. By moving the optical sensors to a radial or ulnar site, it is possible to better utilise PPG signals at red wavelengths and obtain SpO2 sensors with stronger performance. This results in more accurate measurements, for example of heart rate, where prior art monitors located at the back of the wrist typically use green light to access the surface capillaries and utilize the higher absorption of hemoglobin in the green wavelength range. Although red wavelengths are known for SpO2 measurements, this typically takes place at the fingertip of a user, because of the significantly higher vascularization in that location.

A smart strap according to one or more embodiments of the present invention would provide many cardiovascular parameters such as Heart Rate (HR), Heart Rate Variability (HRV), SpO2, Blood Pressure (BP). The strap may rely on a small form factor PIC, application specific integrated circuit (ASIC) and flexible electronic substrate. It is envisioned that the data for measuring the parameters can be obtained with just 2 or 3 laser wavelengths in the red and NIR regions by combining SPG and PPG information. Space is required in the strap for Bluetooth, battery, and other features normal in such a wearable device.

Optionally, the optical sensor may further comprise one or more additional light sources. In this way, the light source is configured to be capable of operating at more than two wavelengths. By providing multiple wavelengths at the sensor, it would be possible to carry out co-oximetry readings. A co-oximeter may use six or more wavelengths to measure the oxygen carrying state of haemoglobin in the blood of a user.

According to one or more embodiments of a second aspect of the present invention, there is provided, a wearable device comprising an optical sensor module according to any one of the embodiments herein.

Optionally, the wearable device may further comprise one or more additional optical sensor(s), the one or more optical sensors corresponding to the optical sensor(s) of any one of the embodiments described herein. This may, for example provide a device capable of performing co-oximetry.

According to one or more embodiments of a third aspect of the present invention, there is provided, a strap (a "smart strap") comprising an optical sensor module according to any one or more of the embodiments described herein.

According to one or more embodiments of a fourth aspect of the present invention, there is provided a wearable device comprising two or more bio-monitoring circuits, each bio-monitoring circuit comprising a respective light source and sensor. Such a wearable device could incorporate any one or more of the optional features described herein.

According to one or more embodiments of a fifth aspect of the present invention, there is provided a strap for a wearable device, the strap comprising two or more bio-monitoring circuits, each biomonitoring circuit comprising a respective light source and sensor. Such a strap could incorporate any one or more of the optional features described herein.

In some embodiments, a wearable device includes a first optical sensor module, the first optical sensor module including an image sensor configured to receive light from biological tissue; a photodiode configured to receive light from the tissue; a light source including a laser and being configured to illuminate, through the tissue, each of the image sensor and the photodiode, a distance between the image sensor and the photodiode being less than 50% of the distance between the image sensor and the light source; and at least one processing circuit configured to process first data corresponding to a first light signal received by the image sensor from the light source to generate a speckleplethysmography (SPG) measurement, and to process second data corresponding to a second light signal received by the photodiode from the light source to generate a photoplethysmography (PPG) measurement.

In some embodiments, the light source is configured to illuminate the tissue with only coherent light.

In some embodiments, the light source is the only light source in the first optical sensor module.

In some embodiments, the image sensor and the photodiode are each spaced apart from the first laser by a substantially same distance.

In some embodiments, one of the image sensor and the photodiode is positioned between the laser and the other one of the image sensor and the photodiode.

In some embodiments, the at least one processing circuit is configured to cause the image sensor and the photodiode to concurrently capture the first light signal and the second light signal, respectively.

In some embodiments, the light source is configured to selectively illuminate the tissue with coherent light or incoherent light; the at least one processing circuit is configured to: during a first time period, cause the light source to illuminate the tissue with coherent light, and to cause the image sensor to capture the first light signal from the light source; and during a second time period, cause the light source to illuminate the tissue with incoherent light, and to cause the photodiode to capture the second light signal from the light source.

In some embodiments, the light source is configured to selectively generate the incoherent light by selectively applying one or more speckle mitigation techniques to coherent light generated by the laser.

In some embodiments, the laser is selectively operable in a first state, wherein light generated by the laser is coherent, and in a second state, wherein light generated by the laser is incoherent.

In some embodiments, the image sensor is a first image sensor and the photodiode is a first photodiode, and the first optical sensor further comprises a second image sensor and a second photodiode, the light source being configured to illuminate, through the tissue, each of the second image sensor and the second photodiode, and a distance between the second image sensor and the second photodiode being less than 50% of the distance between the first image sensor and the light source In some embodiments, the photodiode is configured to perform at least one of in-pixel ambient light subtraction or in-pixel DC light subtraction.

In some embodiments, a wearable device includes a first optical sensor module, the first optical sensor module including: an image sensor configured to receive light from biological tissue; a light source including a laser and being configured to illuminate, through the tissue, the image sensor; and at least one processing circuit configured to process first data corresponding to a first light signal received by the image sensor from the light source to generate a speckleplethysmography (SPG) measurement, and to process second data corresponding to a second light signal received by the image sensor from the light source to generate a photoplethysmography (PPG) measurement, wherein the image sensor is configured to perform in-pixel DC light subtraction.

In some embodiments, a photosensitive surface of the image sensor configured to capture light has an area of less than 30 $mm^2$ and an analog to digital converter with 16 or fewer bits.

In some embodiments, the light source is configured to selectively illuminate the tissue with coherent light and incoherent light; and the at least one processing circuit is configured to: during a first time period, cause the light source to illuminate the tissue with coherent light, and to cause the image sensor to capture the first light signal from the light source; and during a second time period, cause the light source to illuminate the tissue with incoherent light, and to cause the image sensor to capture the second light signal from the light source.

In some embodiments, the light source is configured to selectively generate the incoherent light by selectively applying one or more speckle mitigation techniques to coherent light generated by the laser.

In some embodiments, the laser is selectively operable in a first state, wherein light generated by the laser is coherent, and in a second state, wherein light generated by the laser is incoherent.

In some embodiments, the second light signal is the same as the first light signal, and wherein the at least one processing circuit is configured to, during a first time period, cause the light source to illuminate the tissue with only coherent light, and cause the image sensor to capture the first light signal from the tissue, and wherein the at least one processing circuit is configured to generate both the SPG measurement and the PPG measurement based on data corresponding to the first light signal.

In some embodiments, the light source is the only light source in the optical sensor module, and the image sensor is the only light-capturing component in the optical sensor module.

In some embodiments, the wearable device includes a first optical sensor module, the first optical sensor module including: an image sensor configured to receive light from biological tissue; a light source including a laser, the light source being configured to selectively generate coherent and incoherent light and to illuminate, through the tissue, the image sensor; and at least one processing circuit configured to process first data corresponding to a first light signal received by the image sensor from the light source to generate a speckleplethysmography (SPG) measurement, and to process second data corresponding to a second light signal received by the image sensor from the light source to generate a photoplethysmography (PPG) measurement.

In some embodiments, the light source is configured to selectively generate the coherent and incoherent light by selectively applying one or more speckle mitigation techniques to light generated by the laser.

Further optional features of embodiments of the invention are set out below.

BRIEF DESCRIPTION OF THE DRAWINGS

Embodiments of the invention will now be described by way of example with reference to the accompanying drawings in which.

DETAILED DESCRIPTION

SPG signals are obtained from blood flow speed and are generally of larger magnitude than PPG signals at the same wavelength. Additionally, because the SPG signal is obtained primarily from deeper lying vasculature with faster flow, it is less impacted by applied pressure. The SPG signal is comprised of very sharp peaks when collected at >20 Hz and preferably >100 Hz frame rate and so provides an excellent means of measuring HR. A cardiovascular module that combines SPG and PPG signals may provide numerous cardiovascular metrics including blood pressure, SpO2, arterial stiffness, heart rate, heart rate variability, atrial fibrillation, bradycardia, and tachycardia with just red and "IR" sources. Therefore, a green LED and/or dedicated detector for visible light is not required, which saves both battery consumption and space. Furthermore, the blood flow (SPG) measurement is very sensitive to motion and provides signals that may be interpreted as steps, gestures, or other movement-related phenomena. Thus, the module may or may not include an accelerometer.

Since the hemoglobin absorption band is quite steep in the region of 600-700 nm, SpO2 accuracy depends on the accuracy of the wavelength of the red light. Devices that utilize LEDs, with resulting broadband emission and sensitivity to temperature, may come out of calibration and give erroneous results. SPG signals require a coherent laser as light source. Lasers have much narrower emissions and less sensitivity to temperature, thereby providing a more accurate SpO2 over a wide range of conditions. Note that the "IR" light source (>800 nm) may be broader because haemoglobin absorption is relatively flat in the region 830-900 nm.

The image sensor can incorporate methods of in-pixel cancellation of DC light signals (from non-pulsatile light) or light from the ambient environment. In some embodiments, an event camera sensor may be used in place of a conventional image sensor for the detection of the SPG and PPG signals. Such a sensor offers advantages in lower power usage and processing requirements due to its capability of providing pixel change updates instead of full frame updates.

In some embodiments, the invention includes, but is not limited to a cardiovascular module that provides blood pressure, SpO2, arterial stiffness, heart rate, heart rate variability, atrial fibrillation, bradycardia, and tachycardia parameters, in a wearable, compact form factor. This module is optimized for both PPG and SPG signal collection to obtain robust measurements.

Figure 1:
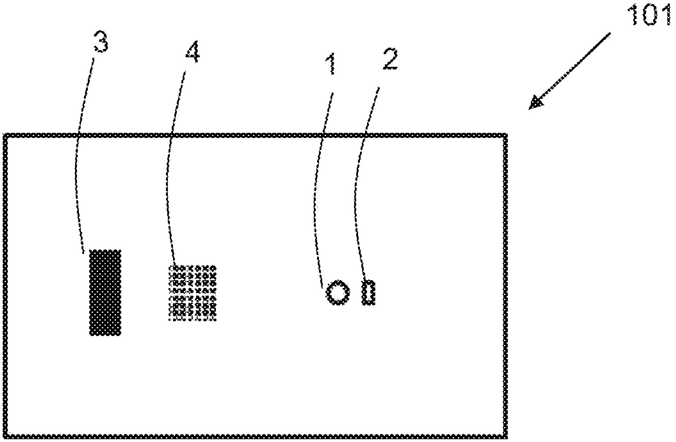
FIG. 1 shows a schematic diagram of an optical sensor module according to an embodiment of the present invention.

FIG. 1 shows an optical sensor module 101, comprising a first light source 1, for illuminating the human tissue for use with SPG measurements. In this embodiment, the first light source is a laser having sufficient coherence length to acquire SPG signals (e.g. vertical-cavity surface-emitting laser (VCSEL), distributed feedback (DFB) diode, distributed Bragg reflector (DBR) diode, volume holographic (VHG) diode, discrete mode (DM) diode (e.g., a discrete mode laser diode)). The tissue may be the tissue of a subject, to whom the optical sensor module 101 (or another optical sensor module described herein) may be attached (e.g., by a strap, or by adhesive).

The optical sensor module also includes a second light source 2 for illuminating the human tissue for use with PPG measurements. In the embodiment shown, the second light source takes the form of an infra-red LED (e.g. having a center wavelength of 830-980 nm).

Including the second light source in the form of an LED may be advantageous as it is less susceptible to error due to wavelength drift owing to the flat hemoglobin spectrum in that region.

A plurality of optical sensor(s) is also located on the optical module for receiving light from the illuminated human tissue. In this embodiment, these sensors include a photodiode, 3 and a CMOS image sensor, 4. The photodiode may take the form of a large area photodiode with DC subtraction electronics. Electronics for the photodiode are present and may be optimized for PPG data collection to obtain SpO2 whereas the CMOS sensor may be utilized for the SPG signal collection to obtain BP and other cardiovascular parameters. This embodiment does not contain a green LED, although it would be possible to adapt it (not shown) to include a green or other wavelength LED or laser either in addition, or as a replacement to the components shown in FIG. 1.

Figure 2:
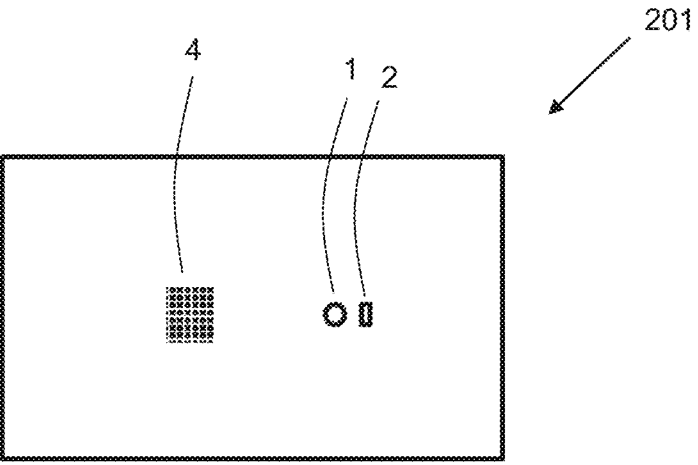
FIG. 2 shows a schematic diagram of an optical sensor module according to a further embodiment of the present invention.

An optical sensor module, 201 according to a second embodiment is described below in relation to FIG. 2, the second embodiment, differing from the embodiment of FIG. 2 in that the photodiode 3 is removed, and the PPG signal is instead obtained using an image sensor.

The image sensor may be a charge-coupled device (CCD), a CMOS image sensor (CIS), or an implementation of a CCD or CIS incorporating an in-pixel DC (non-pulsatile) or ambient light subtraction method such as but not limited to auto-zeroing and chopping, common mode reset, minimum charge transfer, or dual transfer gate architecture.

Alternatively, the image sensor may be an event image sensor (EIS) which produces asynchronous pixel updates according to defined pixel intensity changes as opposed to conventional synchronous frame-based CCD or CIS sensors.

Figure 3:
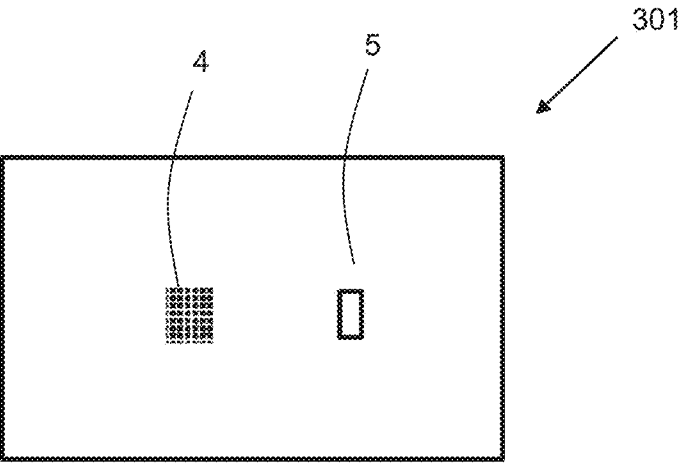
FIG. 3 shows a schematic diagram of an optical sensor module according to a further embodiment of the present invention.

A third embodiment of an optical sensor module 301 is described below with reference to FIG. 3. In this embodiment, both the first and second light source are lasers. The module comprises only the image sensor described in the second embodiment and a photonic integrated chip (PIC) 5 containing at least two lasers, one laser having a red wavelength and one laser having a NIR/IR wavelength. Red wavelength may be taken to be light with a wavelength from 620 nm to 800 nm. NIR/IR may be taken to be light with a wavelength of 800 nm to 1000 nm. The PIC may, in addition, contain multiple laser wavelengths to also perform CO-oximetry (carboxyhemoglobin, methemoglobin, etc). As with the embodiment of FIG. 2, a single image sensor is used to detect both PPG and SPG signals.

Any one or more of the embodiments described herein may utilize temporary speckle mitigation techniques (e.g., one or more temporary speckle mitigation techniques) for the collection of the PPG signal obtained from a photodiode, such as a deformable mirror to rapidly adjust optical pathlengths, an optical phase array, raster scanning, angle scanning, wavelength scanning or broadening, reduced coherence operation, or any combination thereof. In some embodiments, reduced coherence operation includes causing a laser to operate in multiple modes simultaneously to provide incoherent light. This may include manipulation of current and/or temperature to result in multimode behavior. For example, an optical sensor module (e.g., a light source of the optical sensor module) may be configured to controllably modify the current provided to the laser and/or the temperature of the laser to cause the laser to operate in the multiple modes. This may improve SNR as it reduces speckle noise from the intensity signal, which is more important as the size of the sensor/detector is reduced. Additionally, or alternatively, multiple photodiode acquisitions of the laser signal may be collected and averaged to improve SNR.

Any one or more of the embodiments may also include a multi-aperture array in front of the image sensor to improve SNR while maintaining the appropriate speckle to pixel ratio by virtue of the aperture diameters and distance from the sensor. Such a sensor does not require a lens to obtain the appropriate speckle to pixel ratio, although a lens or lens array may be used in conjunction with the aperture plate.

It is to be understood that the embodiments described are not limitations, e.g. green, blue, yellow, or other wavelength LEDs or lasers may be included and any LED may be replaced with a laser. The SPG signal requires, at minimum, one laser of any wavelength be present in the system along with at least one image sensor. Alternatively, in place of an image sensor that is required for speckle spatial contrast measurements, the SPG signal may be obtained by diffuse correlation spectroscopy (DCS) or interferometric diffuse correlation spectroscopy (iDCS). DCS or iDCS requires either a photodiode or balanced receiver with >500 kHz sampling rate or a single photon counting avalanche detector (SPAD) detector.

Additional modalities may be added to this module, such as ECG (electrocardiogramsor(s), which may be utilized in addition to the SPG and/or PPG signals to calculate pulse arrival times to aid in BP estimations. ECG may also be utilized for certain arrythmia detections as part of the suite of cardiovascular parameters.

Figure 4A:
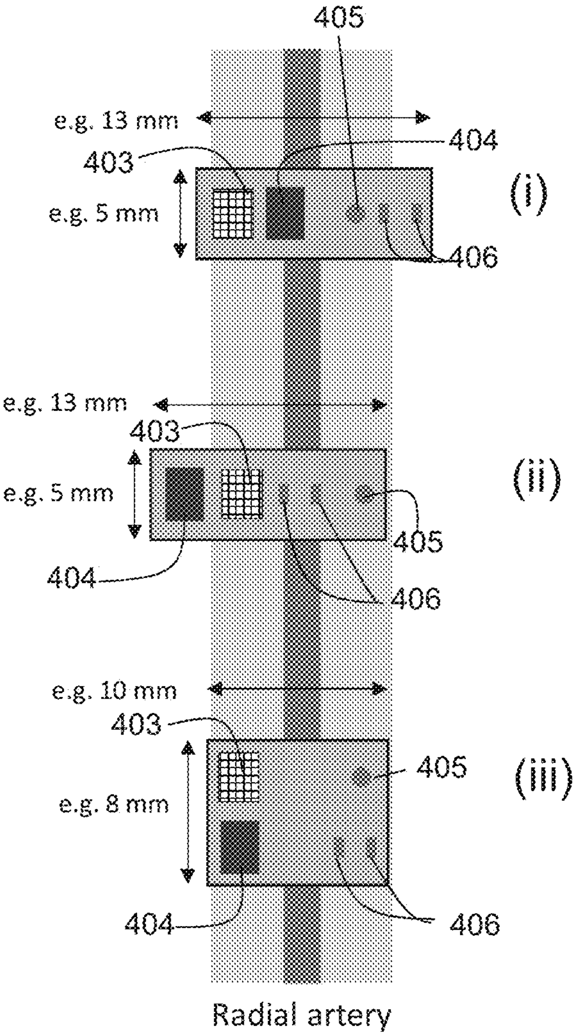
FIGS. 4A and 4B each show a schematic diagram of three further optical sensor modules according to further embodiments of the present invention.
Figure 4B:
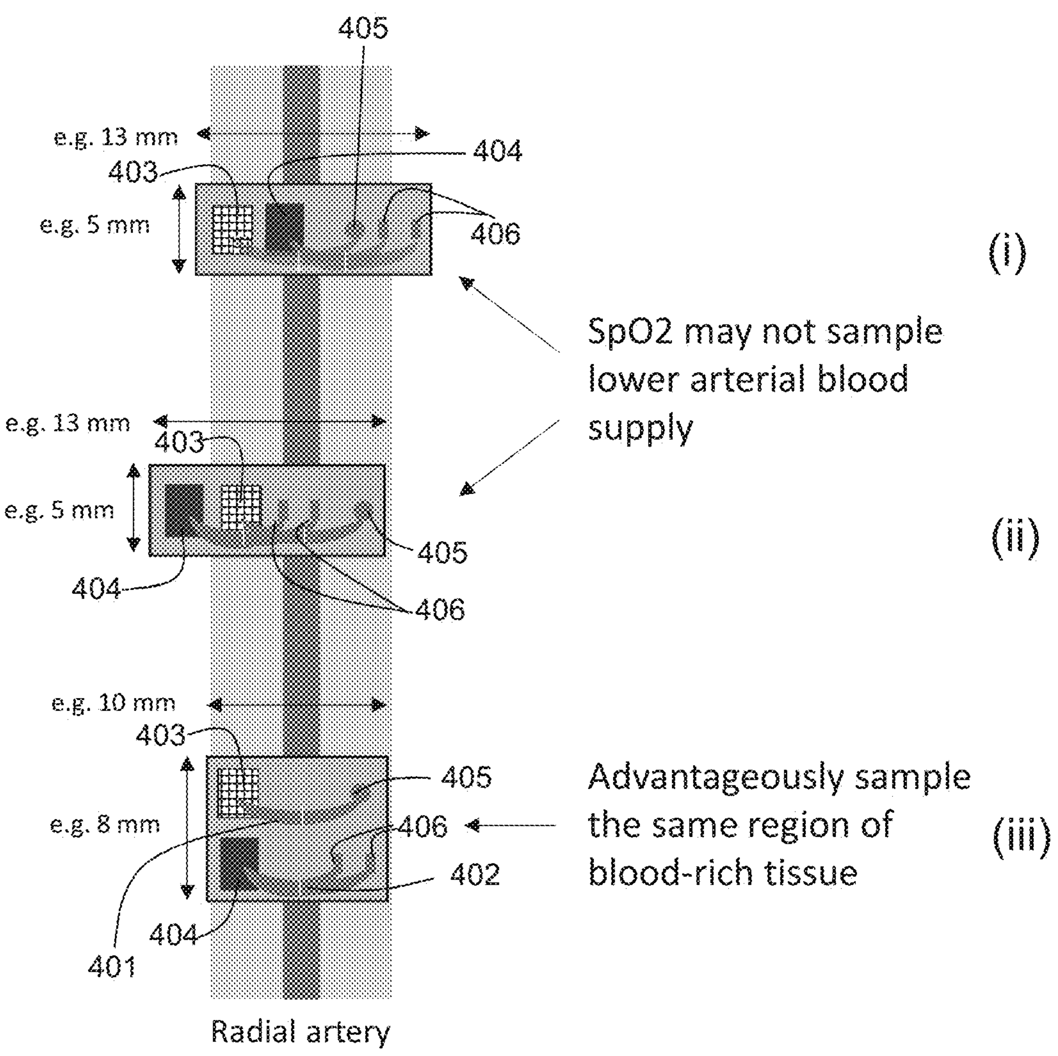

Three further optical modules are shown in FIGS. 4A and 4B. FIG. 4B differs from FIG. 4A in that it shows the link between each light source and its respective detector. Each module ((i)(ii), (iii)) includes an image sensor 403 (e.g. a CMOS image sensor (CIS)), a second sensor 404 (e.g. a photodiode), a laser 405 (e.g. a VCSEL), and one or more LEDs 406 (e.g. a red and an infra-red LED). A module may take the form of discrete components mounted to a printed circuit board assembly (PCBA). Example dimensions are shown and are approximate, based on discreet component sizes. However, it is important to note that these are only illustrative examples, and that other sizes would be possible.

Placement may be over an artery, 15, such as the radial or arterial artery. The arrangement shown in FIG. 4A (iii) (and corresponding FIG. 4B (iii)) is advantageous as the artery passes in the middle of the space, or "banana" (401, 402) formed between the source and detector for both the SPG and PPG modules. In the particular embodiment shown, the SPG and PPG modules are located separately on the same printed circuit board assembly (PCBA), with the PPG module corresponding to the LED(s) and photodiode, and the SPG module corresponding to the laser (e.g. VCSEL) and the image sensor (e.g. CIS).

It has been found to be advantageous for the modules to be stacked vertically with respect to an artery (i.e. along the artery when in use) in order to maximize light of similar source-detector separation. Again, such an arrangement is shown in FIG. 4A (iii) and FIG. 4B (iii).

Figure 5:
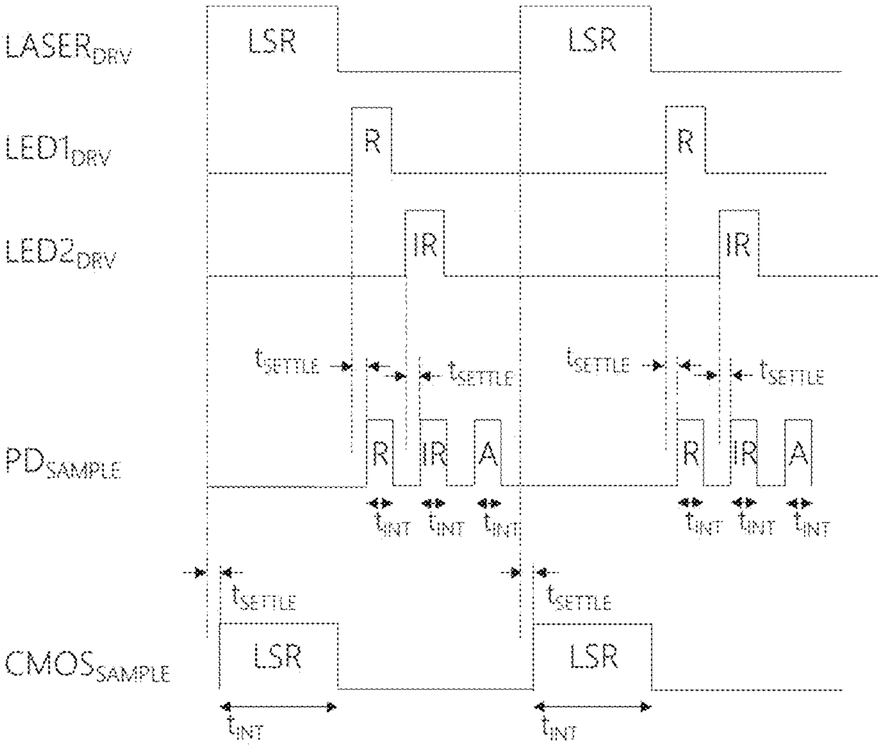
FIG. 5 shows a representation of module operation according to a first example.

A first example of module operation is described below in relation to FIG. 5. In this example, a first laser has a wavelength of 785 nm and separate LEDs having red (660 nm) and IR (900 or 940 nm) wavelengths respectively are also present. This gives a total of three different wavelengths used to interrogate the surface. In the example shown, the LED data acquisition is fitted within the period after camera integration ($t_{INT}$) and before max frame rate, assuming that the camera integration time is less than the period required for max frame rate operation. A time delay $t_{SETTLE}$ is also shown on FIG. 5, this time delay being caused by laser or light intensity stabilisation.

Figure 6:
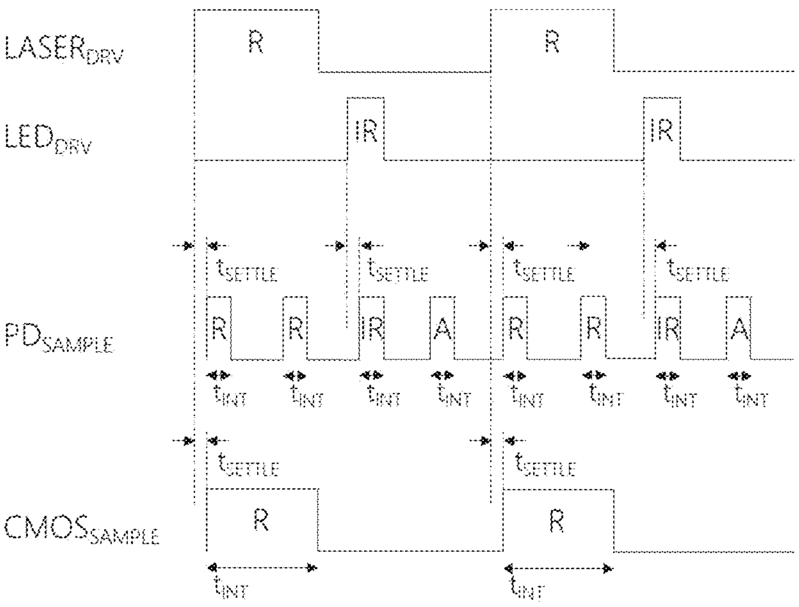
FIG. 6 shows a representation of module operation according to a second example.

A further example is shown in FIG. 6, the optical module comprising a single laser and a single LED, thereby operating at two wavelengths. The laser generates light of a red (e.g. 660 nm) wavelength and the LED generates light of an IR (e.g. 900 or 940 nm) wavelength.

For convenience, operation parameters can be chosen to keep sampling rate of the IR signal the same for the PD and to use the photodiode to acquire multiple collections of the red laser in order to improve SNR due to speckle noise. Depending on the integration times used, it may be possible to carry out two or more red PD acquisitions.

Figure 7:
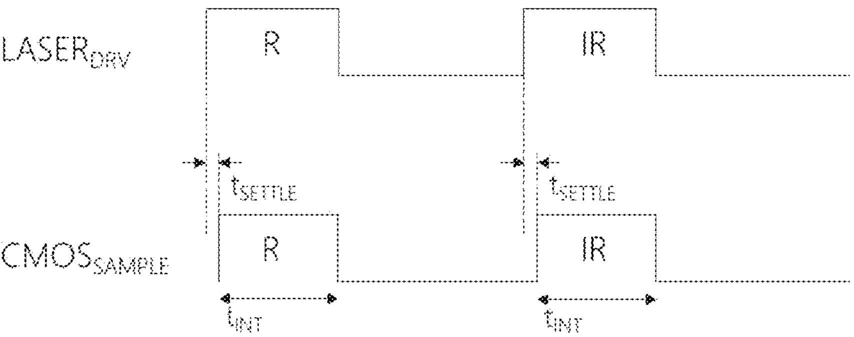
FIG. 7 shows a representation of module operation according to a third example.

A third example of an operation of an optical module is shown in FIG. 7. In this embodiment, the optical module includes a laser module or PIC configured to generate light of two different wavelengths (R and IR), and a single sensor such as a CMOS image sensor. Integration of the signal ($t_{INT}$) by the sensor starts at a time ($t_{SETTLE}$) after the start of the irradiation of the sample by the laser. The PIC may contain two lasers to generate both red (660 nm) and IR (960 nm) light. It is possible that more than two wavelengths may be generated by the PIC, in which case the operation shown in FIG. 7 can be applied, and each wavelength cycled through in a given order.

Figure 8:
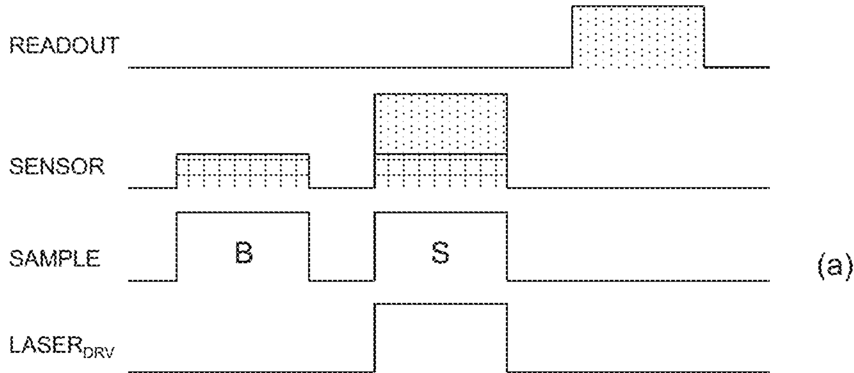
FIG. 8 depicts (a) an illustration of the operation of in-pixel ambient/DC removal, and (b) an illustration of the operation of an event image sensor.
Figure 8:
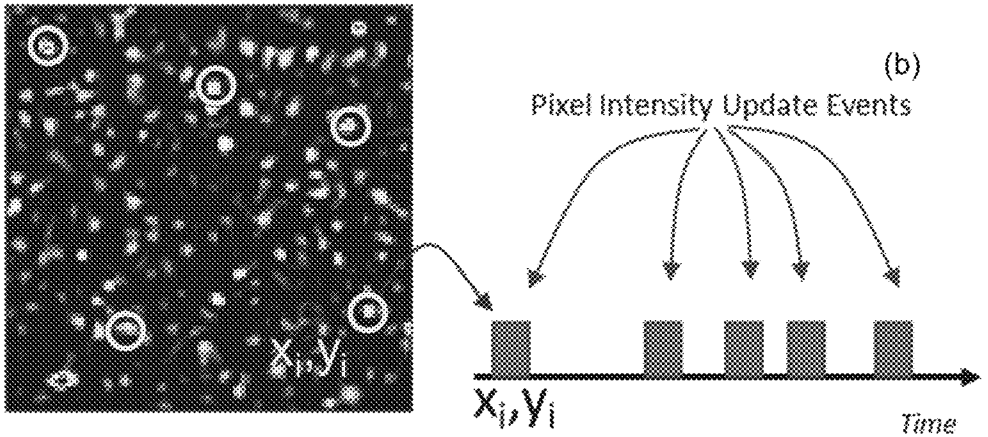

A method by which the sensor can mitigate the effect of ambient background light is shown in FIG. 8.(a). The sensor can sample (SAMPLE-B) the ambient background light with the laser drive off (LASERDRV). The sensor can subsequently sample with the laser on (SAMPLE-S), the resulting reading being a combination of the signal and the ambient background light. Subtraction of the two readings results in a readout (READOUT) consisting of only the contribution of the signal. The subtraction can be accomplished by, but not limited to, in pixel charge subtraction or post-photoconversion voltage subtraction.

An example of a speckle pattern measured by an event based imaging device is shown in FIG. 8.(b). The event based image sensor functions by the detection of discrete changes in pixel intensity (events). The temporal fluctuation of the set of speckle pebbles (xi,yi) translates to the generation of an asynchronous series of pixel events, These events can then be processed by either, but not limited to, integration over a fixed time interval to create a corresponding frame of pixel intensities or in an online fashion by which a histogram of pixel update event rates relates to the temporal fluctuation of the speckle pattern.

Figure 9:
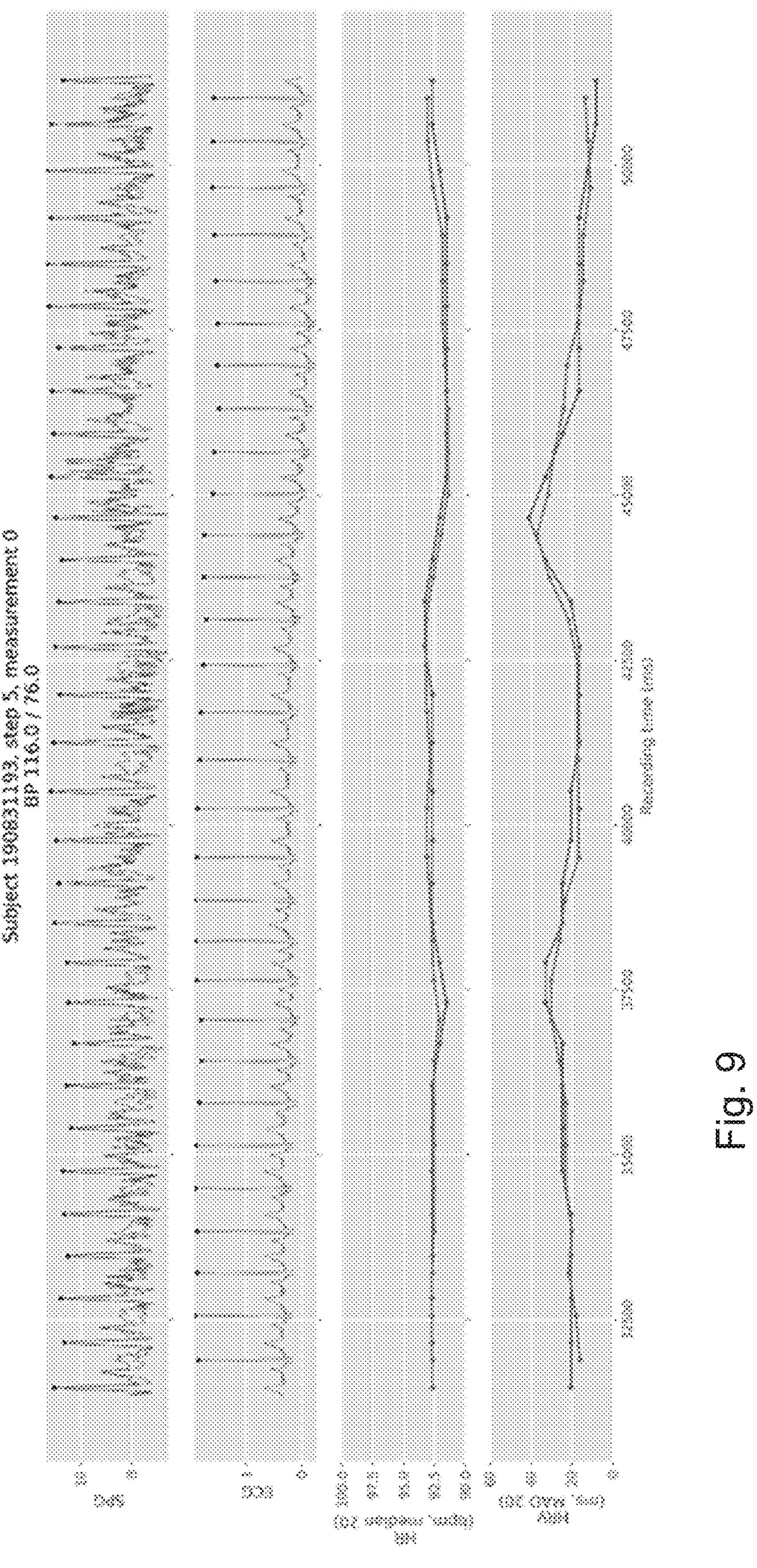
FIG. 9 depicts SPG and ECG data from a first subject.
Figure 10:
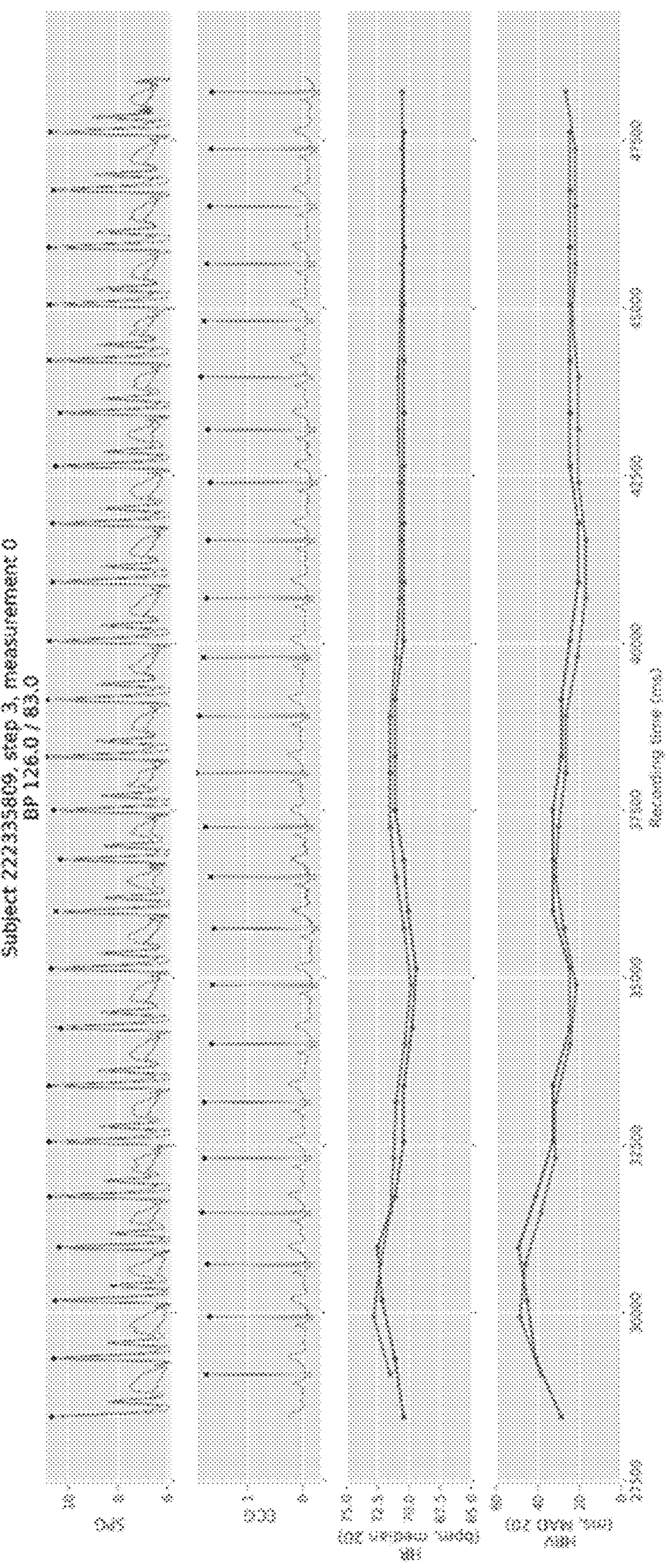
FIG. 10 depicts SPG and ECG data from a second subject.

Examples of SPG (top) and ECG (second from top) data from two subjects are shown in FIGS. 9 and 10 respectively, the data showing equivalency in performance of measuring HR (third from top) and HRV (bottom).

Figure 11:
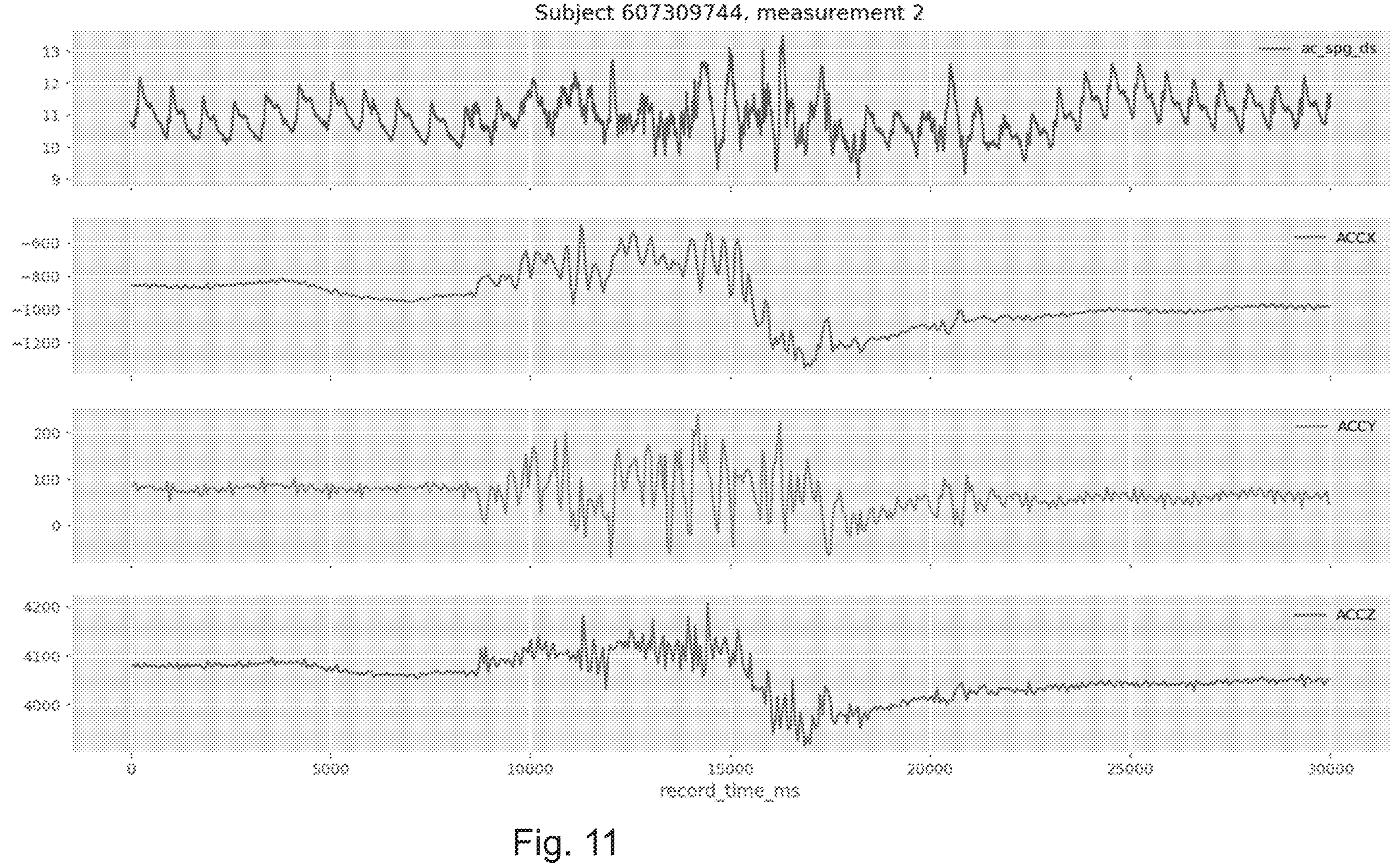
FIG. 11 depicts SPG data from a third subject.
Figure 12:
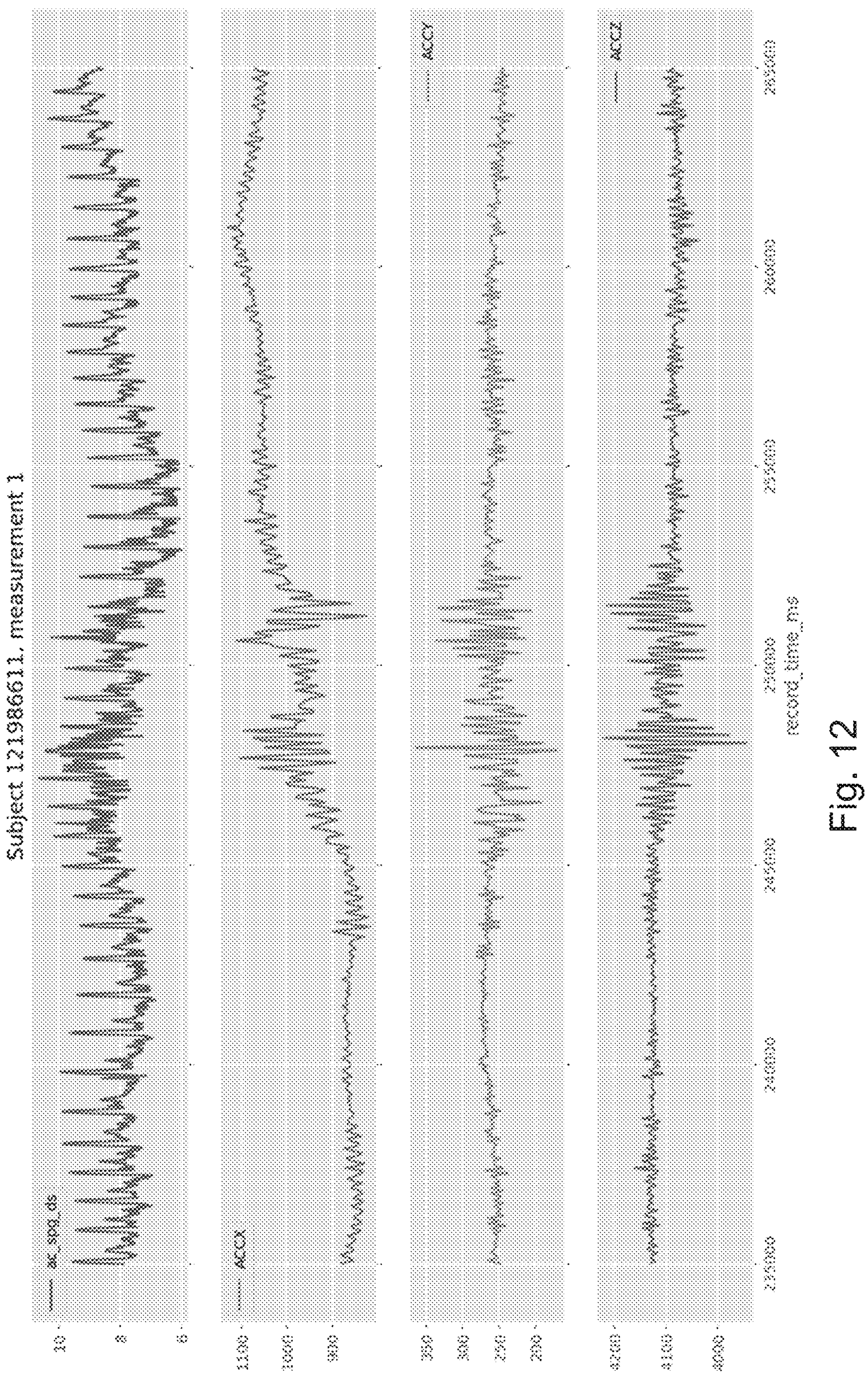
FIG. 12 depicts SPG data from a fourth subject.

Examples of SPG signals (top) contain both high and low-frequency components of accelerometer data (X, Y, and Z axes in second, third, and fourth plots from the top) are shown in FIGS. 11 and 12 for two respective subjects. Motion detection and tracking may be achieved via the SPG signal and without the need for an accelerometer.

Figure 13:
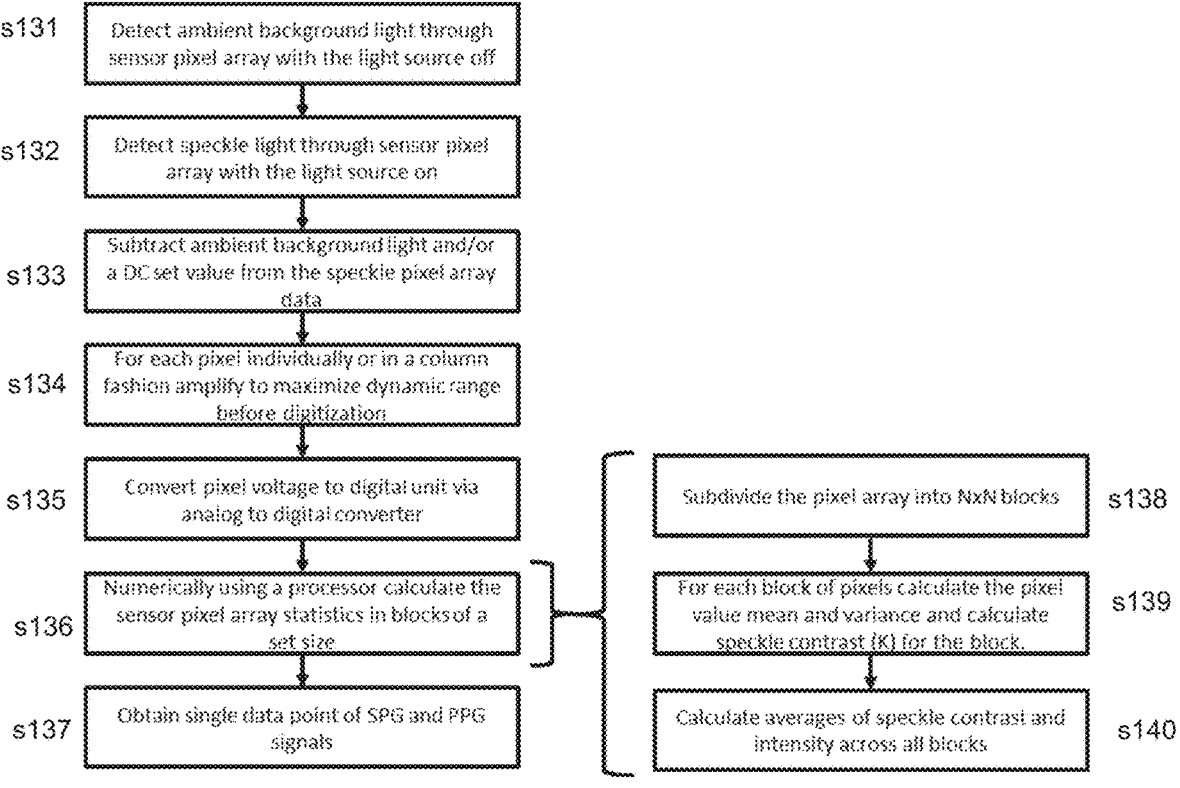
FIG. 13 depicts an example process followed where the optical sensor module of some embodiments of the present invention is configured to carry out pixel array statistics.
Figure 14:
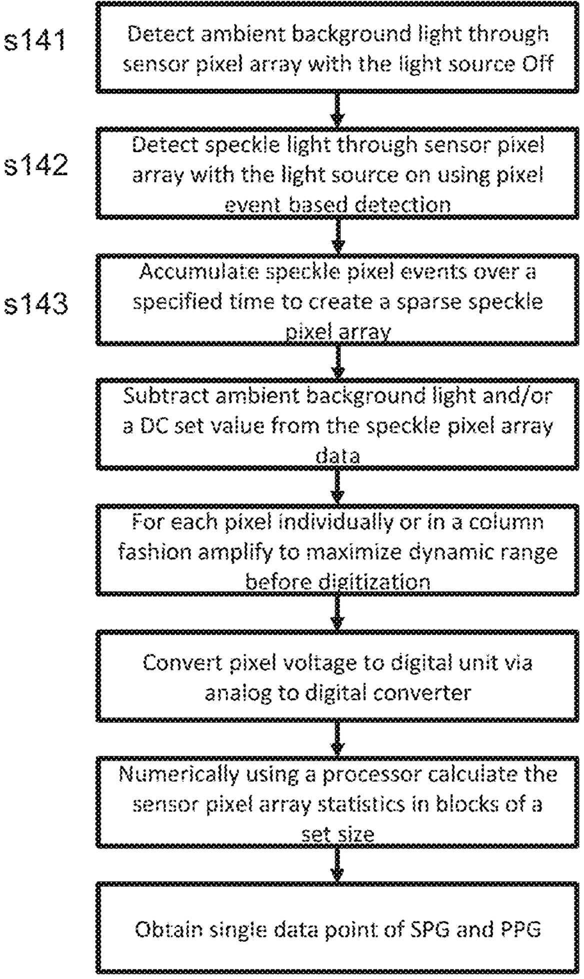
FIG. 14 depicts an example process followed where the optical sensor module of some embodiments of the present invention is configured to carry out event-based detection.

The processing of data from one or more sensor pixel arrays can be better understood with reference to the flow diagrams shown in FIGS. 13 and 14.

In the embodiment shown in FIG. 13, a sensor pixel array is first used to detect ambient background light with the light source turned off (s131). Speckle light is then detected (s132) by the sensor pixel array, when the light source is turned on. Ambient background light can then be subtracted and/or a DC set value can be subtracted from the speckle pixel array data (s133). For each pixel individually, or in a column fashion, amplification (s134) may be carried out to maximize the dynamic range of the data before digitization (s135). At digitization, pixel voltage is converted to digital unit via an analogue to digital converter. A processor may then calculate (s136) the sensor pixel array statistics, and may do so in blocks of a set size. Once these statistics have been calculated, a single data point can be obtained (s137), the single data point corresponding to SPG and PPG signals.

Calculation (s136) of the sensor pixel array statistics may include the steps of: subdividing (s138) the pixel array into N×N blocks; for each block, calculating (s139) the pixel value mean and variance and calculating speckle contrast (K) for the block; and calculating (s140) averages of speckle contrast and intensity across all blocks.

A process including event-based detection is described below in relation to FIG. 14. The process differs from that described above in relation to FIG. 13 in that the first two steps (s131, s132) are replaced by three new steps (s141, s142, s143). Firstly, ambient background light is detected (s141) through the sensor pixel array with the light source off, then speckle light is detected (s142) through the pixel array with the light source on. This may be achieved by pixel event-based detection. Next, speckle pixel events are accumulated (s. 143) over a specified time, to create a sparse speckle pixel array.

In one or more embodiments of the present invention, the optical sensor module is located on a wrist strap 1501 of a wearable device. In some of these embodiments, the optical sensor module is entirely located on a smart strap, the smart strap being a strap that includes all of the electronics and processing required by the optical sensor and can thus function completely separately from any timepiece that is to be connected to the strap. In this way, the smart strap may be used in combination with (e.g. by retrofitting onto) any pre-existing timepiece including analogue timepieces.

Figure 15:
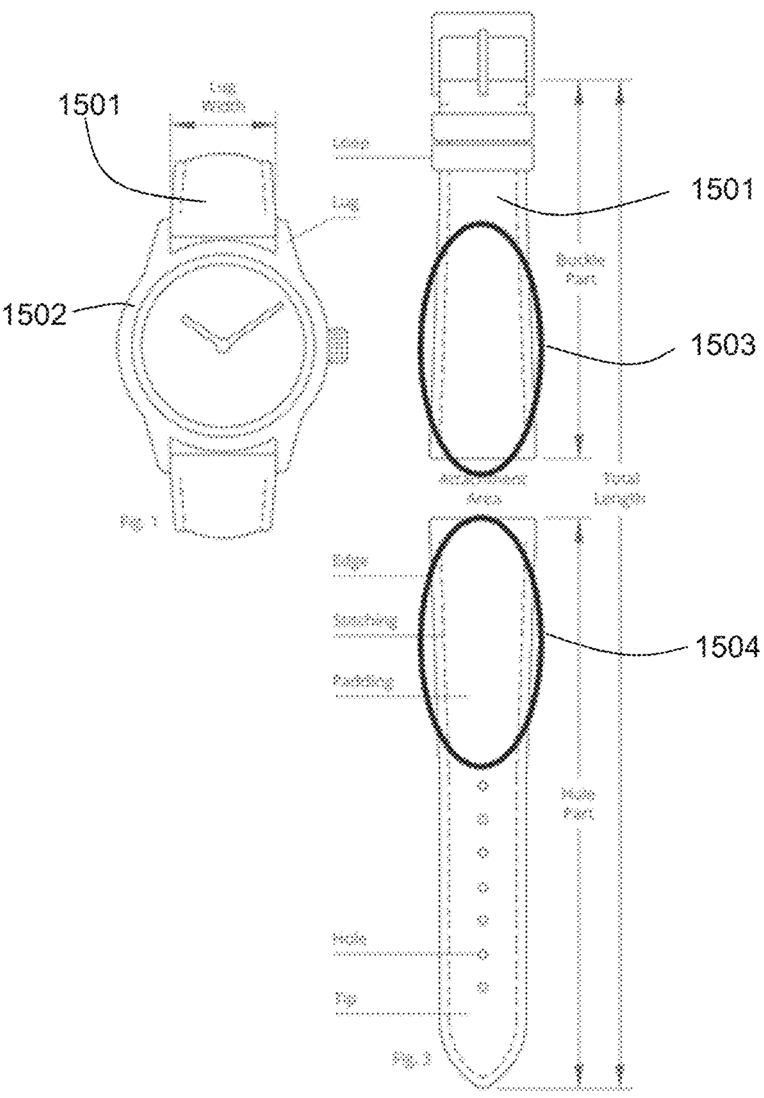
FIG. 15 depicts a smart strap comprising an optical sensor according to some embodiments of the present invention, the smart strap being made of a non-conductive material.

A first smart strap is shown in FIG. 15, the smart strap 1501 being connectable to a timepiece 1502. This embodiment is typical of non-metal (e.g. leather) straps. The optical sensor module may be located within a region 1503, 1504 on one or both sides of the strap such that the optical sensors lie over the radial and/or ulnar artery (arteries) of the user.

Figure 16:
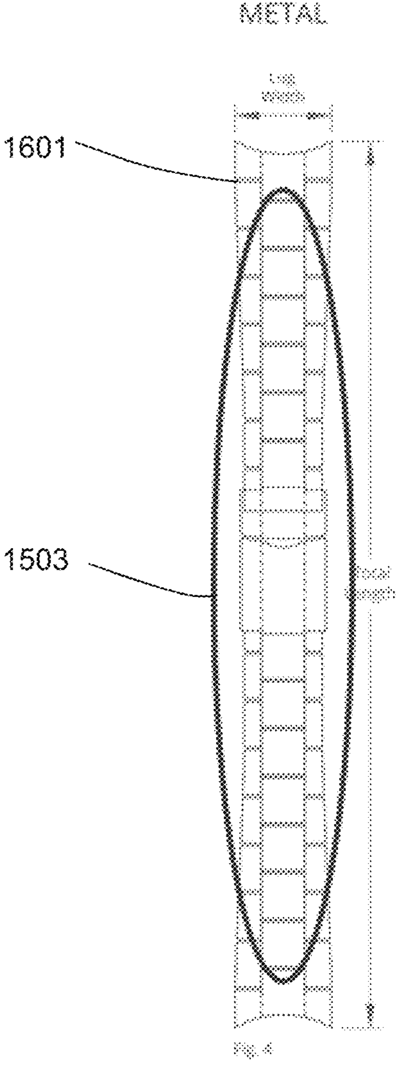
FIG. 16 depicts a smart strap comprising an optical sensor according to some embodiments of the present invention, portions of the smart strap being made of a conductive material.

In an alternative smart strap shown in FIG. 16, the smart strap 1601 is made of a conductive material such as metal. Again, components of the optical sensor module may be located along the strap, and typically along the entire region 1603 of the strap. Any optical sensors of the optical sensor module may be placed so that when the conductive strap (or "portionally conductive" strap, such as a strap having only a portion that is conductive) is in use, being worn by the user, the one or more sensors are located above the radial and/or ulnar artery (arteries) of the user.

On a conductive (or portionally conductive), metal strap, the possibility exists for the sensing and electronic elements such as battery, Bluetooth, etc to be spread out, using the clasp (volar wrist) or other contact points along the strap as an electrical connection It is possible to optimally design a strap using any external material (leather, silicone, plastic, metal) with sensing and electronics fully enclosed within and using the clasp for electrical attachment. The attachment area (dorsal wrist to timepiece/smartwatch) would be standard lug or compression spring or other common attachment mechanism.

Figure 17:
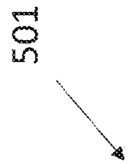
FIG. 17 shows a schematic diagram of an optical sensor module according to some embodiments.
Figure 17:
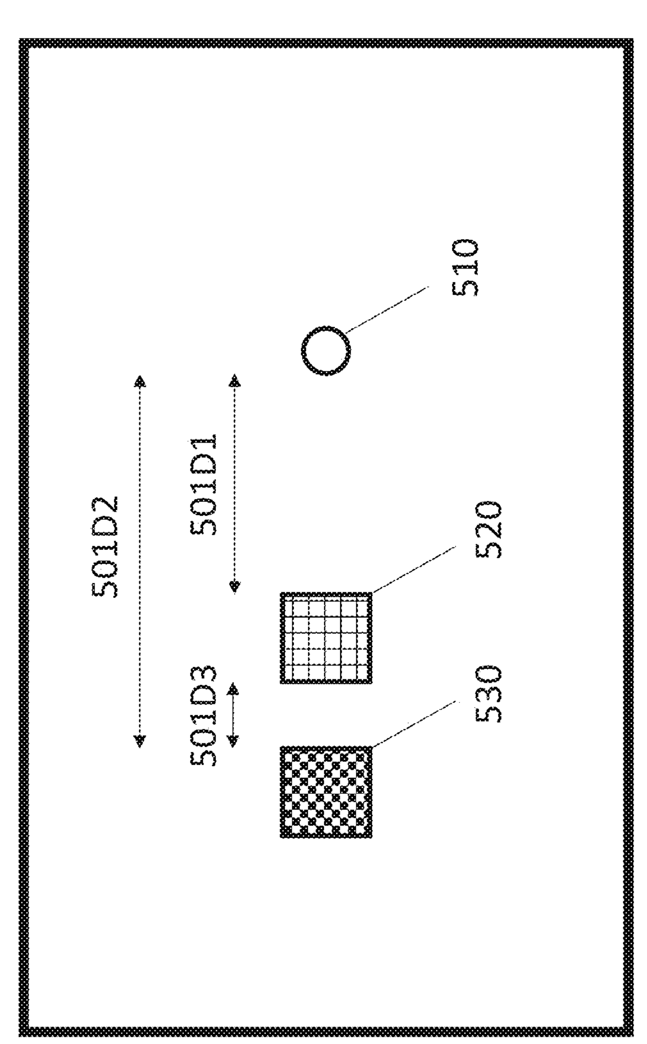
Figure 18:
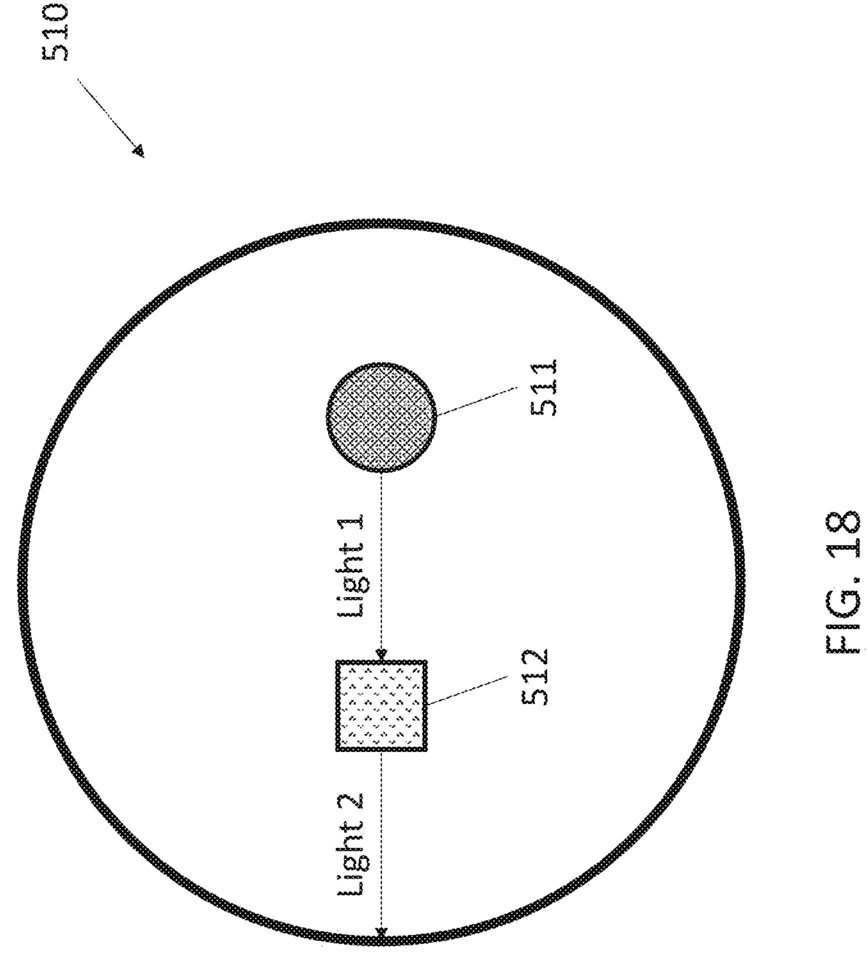
FIG. 18 shows a schematic diagram of a light source of the optical sensor module of FIG. 17 according to some embodiments.

FIG. 17 shows a schematic diagram of an optical sensor module 501 according to some embodiments. FIG. 18 shows a schematic diagram of a light source 510 of the optical sensor module 501 of FIG. 17 according to some embodiments. The optical sensor module 501 may include features similar to, or the same as, features of other optical sensor modules described herein. Therefore, redundant descriptions may be omitted herein.

Referring concurrently to FIGS. 17 and 18, the optical sensor module 501 may include a light source 510, an image sensor 520 (e.g., a CMOS image sensor), a photodiode 530, at least one processing circuit configured to control operations of the optical sensor module 501, and a memory storing instructions that, when executed by the at least one processing circuit, cause the at least one processing circuit to control operations of the optical sensor module 501, including any operation or combination of operations of the optical sensor module 501 described herein or otherwise within the scope of the present disclosure.

The light source 510 may be configured to illuminate tissue (e.g., the skin of a human or of a (non-human) animal), and to illuminate each of the image sensor 520 and the photodiode 530 through the tissue. The image sensor 520 and the photodiode 530 may respectively be configured to receive, through the tissue, first and second light signals from the light source 510 for respectively generating SPG and PPG measurements. The image sensor 520 and the photodiode 530 may respectively include features similar to, or the same as, features of other image sensors and photodiodes described herein. For example, the image sensor 520 and the photodiode 530 may each be configured to perform detector-implemented subtraction, which may include embodiments where the detector or the pixels of the detector (in the case of the image sensor 520) are configured to subtract a DC value. The DC value may be, for example, a current or voltage value corresponding to a measured light signal or that is supplied by the detector (or from outside the detector). For example, detector-implemented subtraction may include ambient light subtraction (e.g., in-pixel ambient light subtraction) and/or DC light subtraction (e.g., in-pixel DC light subtraction). Ambient light subtraction may include measuring a preliminary current or voltage in response to the detector being illuminated with ambient light and without light from the light source 510, capturing a subsequent current or voltage in response to the detector being illuminated with both ambient light and light from the light source 510 at a later time, and subtracting (e.g., subtracting in-pixel) the preliminary current or voltage from the subsequent current or voltage. DC light subtraction may include measuring a preliminary current or voltage in response to the detector being illuminated with light from the light source 510, measuring a subsequent current or voltage in response to the detector being illuminated with the light source 510 at a later time, and subtracting (e.g., subtracting in-pixel) the preliminary current or voltage from the subsequent current or voltage.

In some embodiments, the light source 510 is the only light source of the optical sensor module 501. By using a single light source to illuminate both of the image sensor 520 and the photodiode 530, overlap between (i) the first optical path, from the light source 510 to the image sensor 520 and (ii) the second optical path, from the light source 510 to the photodiode 530 may be increased so that substantially similar tissue is interrogated for both the SPG and PPG measurements. Increasing such overlap can be desirable because an analysis or determination of certain characteristics of the tissue (e.g., performed by the at least one processing circuit of the optical sensor module 501 or by at least one processing circuit (e.g., a processor, such as a microprocessor or microcontroller) separate from the optical sensor module 501) may be based on the combination of the SPG and PPG measurements and may assume that the SPG and PPG measurements interrogated the same tissue. Although this assumption may not be entirely accurate, it can be made approximately correct by causing the first and second optical paths to overlap as much as possible, which may be accomplished by using a single light source. In a comparison embodiment, such as the embodiment shown in FIG. 1, different light sources (the first and second light sources 1 and 2) may be used to obtain the SPG and PPG measurements, which can reduce the overlap between the corresponding optical paths.

As used herein, when a light source is described as being "the only light source in the optical sensor module," this may mean that, on the optical sensor module 501 (or on a wearable device (e.g., the strap of a wearable device) that the optical sensor module 501 is on or part of) there is only one light source that is operably configured to illuminate the tissue. In some embodiments, this may mean that there are no other light sources operably configured to illuminate the tissue within a distance from the light source 510 equal to the product of (i) a first distance 501D1 (e.g., a first smallest distance), which is the distance between the light source 510 and the image sensor 520 (or a second distance 501D2 (e.g., a second smallest distance), which is the distance between the light source 510 and the photodiode 530) and (ii) a set value within a range of 0.1 to 10 (e.g., 0.25, 0.5, 0.75, 1, 2, 3, 4, or 5). In some embodiments, the wearable device may include a plurality of optical sensor modules (e.g., a plurality of the optical sensor modules 501), and each of the optical sensor modules includes only one light source (e.g., only the light source 510).

A third distance 501D3 (e.g., a third smallest distance), which is the distance between the image sensor 520 and the photodiode 530 may be less than 3 mm, for example, less than 2.5 mm, 2 mm, 1.5 mm, 1.0 mm, or 0.5 mm. In some embodiments, the third distance 501D3 is less than the product of the first distance 501D1 (or the second distance 501D2) and a set value less than 1, 0.5, 0.25, 0.20, 0.15, 0.10, or 0.05. By reducing the third distance 501D3 and keeping the image sensor 520 and the photodiode 530 close together, the first and second optical paths may overlap more than if the third distance 501D3 is larger.

In the embodiment depicted in FIG. 17, the image sensor 520 is positioned between the light source 510 and the photodiode 530, and the second distance 501D2 is larger than the first distance 501D1. In some other embodiments, the photodiode 530 may be positioned between the light source 510 and the image sensor 520, and the first distance 501D1 may be larger than the second distance 501D2. Positioning one of the image sensor 520 and the photodiode 530 between the light source 510 and the other one of the image sensor 520 and the photodiode 530 may cause the SPG and PPG measurements to interrogate substantially overlapping tissue volumes that are at somewhat different average depths.

In some embodiments, the image sensor 520 and the photodiode 530 are spaced apart from the laser 510 by substantially the same distance. For example, the first and second distances 501D1 and 501D2 may be substantially the same (e.g., within 20%, 15%, 10%, 5%, 2%, or 1% of each other). For example, instead of the light source 510, the image sensor 520, and the photodiode 530 being aligned along the horizontal (left-right) direction as shown in FIG. 17, the image sensor 520 and the photodiode 530 may be aligned with each other along the vertical (up-down) direction shown in FIG. 17, and may be spaced apart from the light source 510 in the horizontal direction shown in FIG.

17. In such embodiments, the SPG and PPG measurements may interrogate tissue volumes that are at substantially similar depths and that are somewhat spaced apart along the transverse direction (e.g., somewhat spaced apart along the vertical direction).

The light source 510 may be configured to provide only coherent light, or the light source 510 may be configured to selectively provide (e.g., to selectively toggle between providing) coherent light and incoherent light. The incoherent light may be spatially incoherent, temporally incoherent, or both spatially incoherent and temporally incoherent. While coherent light can be used for obtaining an SPG measurement, coherent or incoherent light can be used for obtaining a PPG measurement. In some embodiments where the light source 510 is configured to provide only coherent light, the coherent light may be used for obtaining both the SPG and PPG measurements. In embodiments where the light source 510 is configured to selectively provide coherent light and incoherent light, the coherent light may be used for obtaining the SPG measurement, while the incoherent light may be used for obtaining the PPG measurement.

A light source configured to selectively provide coherent and incoherent light can be more expensive and complex than a light source configured to provide only coherent light. Therefore, using a light source configured to provide only coherent light can reduce costs, rate of failure, and complexity of operation of the optical sensor module. On the other hand, incoherent light can reduce the effects of speckle noise on the PPG measurement, which can be particularly important if relatively few speckles (e.g., less than 100 or 500 speckles) illuminate the photodiode sensing area used in the optical sensor module. Therefore, a light source configured to selectively provide coherent and incoherent light may provide more accurate PPG measurements than a light source that is configured to provide only coherent light.

The light source 510 may include (e.g., be) a laser 511 (e.g., a single-wavelength laser) and may include or omit one or more speckle mitigation elements 512. The one or more speckle mitigation elements 512 may be configured to selectively implement one or more speckle mitigation techniques on light generated by the laser 511 so that the light source 510 selectively provides incoherent light. For example, the one or more speckle mitigation elements 512 may include one or more speckle mitigation elements described in U.S. Patent Application Publication No. 2023/0228989, titled "Deformable Membrane For Speckle Mitigation", which is incorporated herein by reference. In some embodiments, the incoherent light resulting from the one or more speckle mitigation techniques applied to the light generated by the laser 511 may be temporally coherent. For example, the laser 511 may be configured to generate coherent first light Light 1, and the one or more speckle mitigation elements 512 may be configured to receive and convert (e.g., via modulation) the coherent first light Light 1 into incoherent second light Light 2. The one or more speckle mitigation elements 512 may include elements configured to implement any one or more speckle mitigation techniques described herein. The one or more speckle mitigation elements 512 may be separate from the laser 511 or form part of the laser 511 (e.g., be integral components of the laser 511).

The laser 511 may be configured to generate only coherent light, or the laser 511 may be configured to selectively generate (e.g., selectively toggle between generating) coherent light and incoherent light. For example, the laser 511 may be selectively operable in a first state, wherein light generated by the laser 511 is coherent, and in a second state, wherein light generated by the laser is incoherent. In some embodiments, the laser 511 is a vertical-cavity surface-emitting laser (VCSEL) that is configured to generate incoherent light when a power input (e.g., a drive current) into the laser is above a threshold power value, and to generate coherent light when the power input into the laser is below the threshold power level. In some examples, the laser may be a type having a higher threshold current, the laser being configured to emit incoherent light (e.g., amplified spontaneous emission light) when receiving a drive current below the threshold current and to emit coherent light when receiving a drive current above the threshold current. The at least one processing circuit (e.g., a processor) may be configured to control operations of the light source 510, the image sensor 520, and the photodiode 530.

The at least one processing circuit may further be configured to control other operations of the optical source module 501, such as processing first and second data corresponding to the first and second light signals captured by the image sensor 520 and the photodiode 530 respectively. The first data may be data generated by the image sensor 520 in response to receiving the first light signal and may include, for example, a digitized image generated based on the first light signal. The first data (e.g., the digitized image) may include information about a speckle pattern (e.g., a measured speckle contrast), which can be used to generate an SPG measurement. As used herein, a "measured speckle contrast" is the contrast measured by an imaging detector. It may differ from the true speckle contrast of the light incident on the detector for various reasons, for example because of temporal and spatial averaging inherently performed by each pixel of the detector. The second data may be data generated by the photodiode 530 in response to receiving the second light signal and may include, for example, information about a current generated by the photodiode 530 in response to receiving the second light signal, which can be utilized to generate a PPG measurement. In some examples, the at least one processing circuit may be configured to generate SPG and PPG measurements respectively based on the first and second data, and the at least one processing circuit may be configured to analyze the generated SPG and PPG measurements to determine one or more biological characteristics of the tissue based on the generated SPG and PPG measurements.

The at least one processing circuit may be partially or entirely separate from the light source 510, the image sensor 520, and the photodiode 530. In some embodiments, the at least one processing circuit may form part of at least one of the light source 510, the image sensor 520, or the photodiode 530. For example, the optical sensor module 501 may include a central processing circuit (e.g., a microprocessor or microcontroller) configured to directly control operations of one or more of the light source 510, the image sensor 520, or the photodiode 530, or to send instruction signals to respective processing circuits of the light source 510, the image sensor 520, and the photodiode 530 to indirectly control operations of such components.

Figure 19:
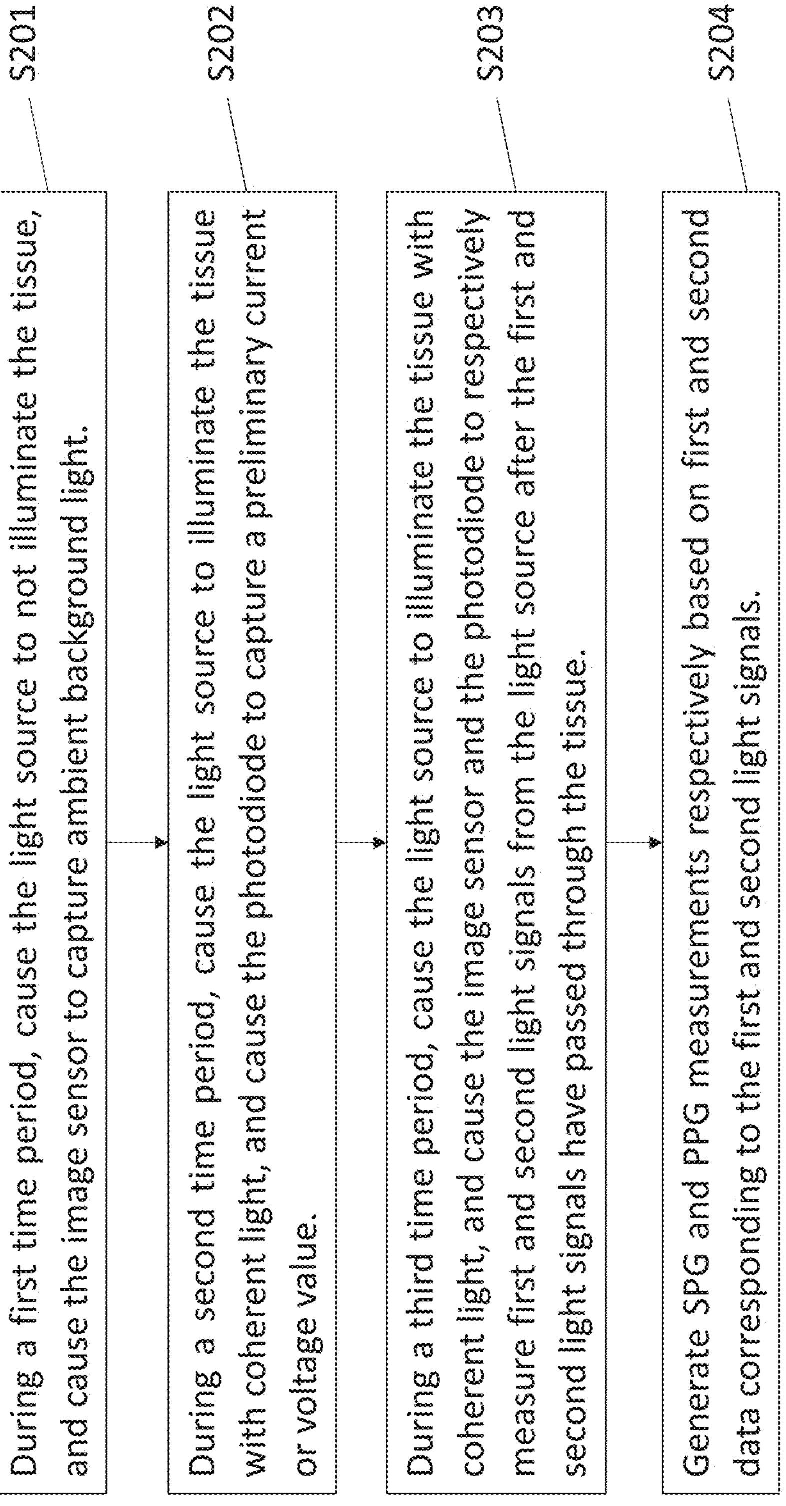
FIGS. 19 and 20 each show operations of the optical sensor module of FIG. 17 according to some embodiments.
Figure 20:
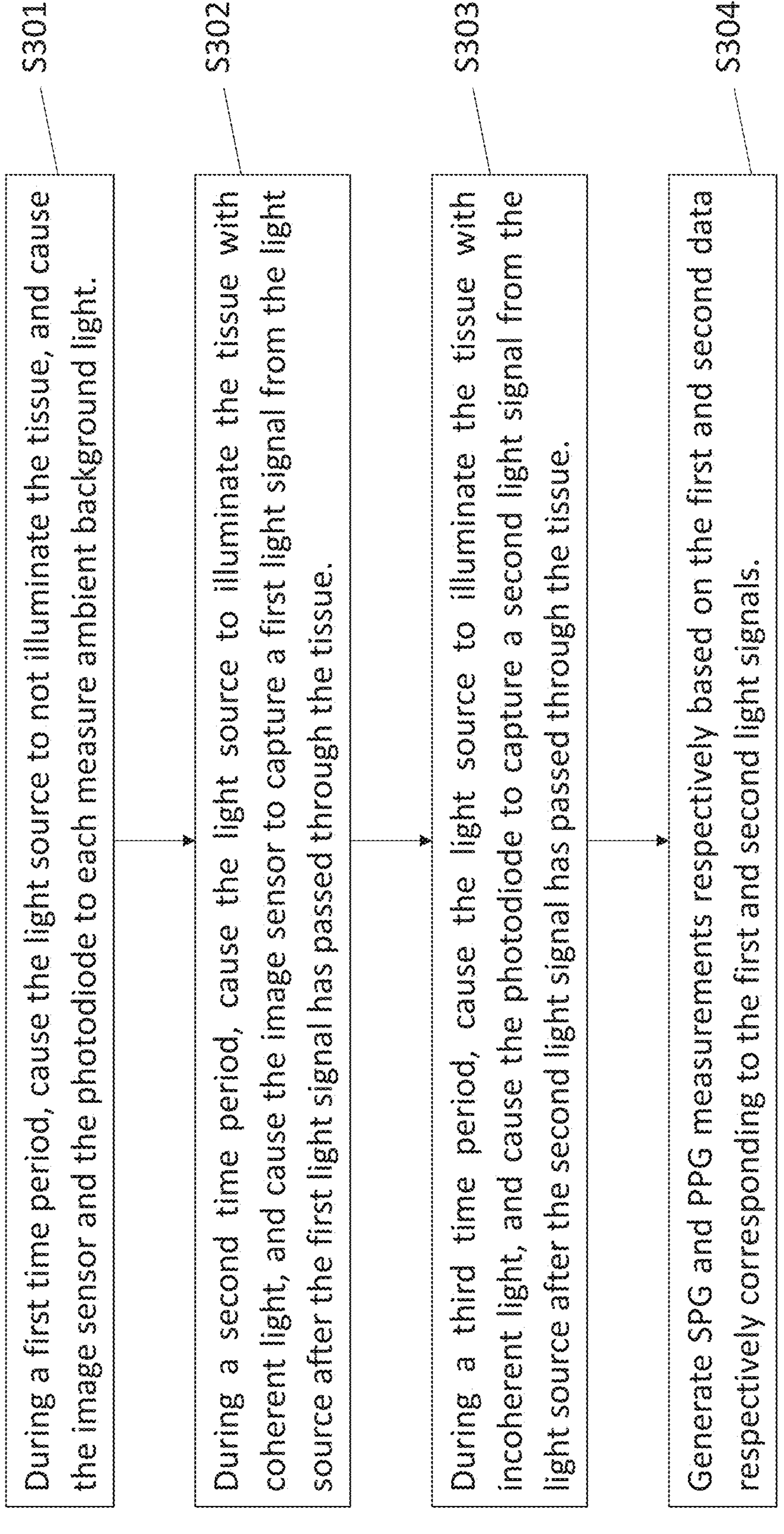

FIGS. 19 and 20 each show operations of the optical sensor module 501 according to some embodiments.

The operations of FIG. 19 may be used, for example, when the light source 510 is configured to only provide coherent light.

In a first operation S201, the at least one processing circuit may be configured to, during a first time period, cause the light source 510 to not illuminate the tissue, and to cause the image sensor 520 to capture an ambient background image. In a second operation S202, the at least one processing circuit may be configured to, during a second time period, cause the light source 510 to illuminate the tissue with coherent light, and cause the photodiode 530 to measure a preliminary light signal reaching the photodiode 530 from the light source 510 through the tissue. The preliminary light signal may be used to obtain a set DC value, which may be subtracted out when generating a PPG measurement. During a third operation S203, the at least one processing circuit may be configured to, during a third time period, cause the light source 510 to illuminate the tissue with coherent light, and cause the image sensor 520 and the photodiode 530 to respectively capture first and second light signals reaching the image sensor 520 and the photodiode 530 from the light source 510 through the tissue. In some embodiments, the image sensor 520 and the photodiode 530 may concurrently (e.g., simultaneously) capture the first and second light signals, respectively. In some other embodiments the image sensor 520 and the photodiode 530 may sequentially capture the first and second light signals. During a fourth operation S204, the at least one processing circuit may be configured to generate SPG and PPG measurements respectively based on first and second data corresponding to the first and second light signals. As described above, the first and second data may be respectively generated by the image sensor 520 and the photodiode 530 based on the first and second light signals received by the image sensor 520 and the photodiode 530.

The captured ambient background image may be subtracted out, in-pixel in the image sensor 520, from the captured first light signal, and the resulting image may be digitized to provide the first data. In some other embodiments, the ambient background image and the first light signal are separately digitized into separate digital images, and the digitized ambient background image is digitally subtracted out from the digitized first light signal image before the resulting image is used to generate the SPG measurement. In some embodiments, a current or voltage based on the captured preliminary light signal, which may be the DC set value, may be subtracted out, in the photodiode 530, from a current or voltage based on the captured second light signal, and the resulting current or voltage may be converted from an analog value to a digital value to provide the second data. In some other embodiments, the currents or voltages obtained by the photodiode respectively from the preliminary light signal and the second light signal are separately converted from analog to digital values, and the digital value of the current or voltage obtained from the preliminary light signal (e.g., the set DC value) is digitally subtracted out from the digital value of the current or voltage obtained from the second light signal before the resulting digital value is used to generate the PPG measurement.

The operations of FIG. 20 may be used, for example, when the light source is configured to selectively provide coherent and incoherent light. Some features of the operations of FIG. 20 may be similar to the features of the operations of FIG. 19. Therefore, redundant descriptions may be omitted herein.

During a first operation S301, the at least one processing circuit may be configured to, during a first time period, cause the light source 510 to not illuminate the tissue, and to cause the image sensor 520 and the photodiode 530 to each capture an ambient background signal. For example, the image sensor 520 may capture an ambient background image, and the photodiode 530 may measure an ambient background value (e.g., a current or voltage corresponding to the ambient background light). During a second operation S302, the at least one processing circuit may be configured to, during a second time period, cause the light source 510 to illuminate the tissue with coherent light, and cause the image sensor 520 to capture the first light signal reaching the image sensor 520 from the light source 510 through the tissue. In some examples, the at least one processing circuit is configured to cause the photodiode 530 to not capture an image during the second time period. During a third operation S303, the at least one processing circuit may be configured to, during a third time period, cause the light source 510 to illuminate the tissue with incoherent light, and to cause the photodiode 530 to capture the second light signal reaching the photodiode 530 from the light source 510 through the tissue. In some examples, the at least one processing circuit is configured to cause the image sensor 520 to not capture a light signal during the third time period. During a fourth operation S304, the at least one processing circuit may be configured to generate SPG and PPG measurements respectively based on first and second data corresponding to the first and second light signals.

Figure 21:
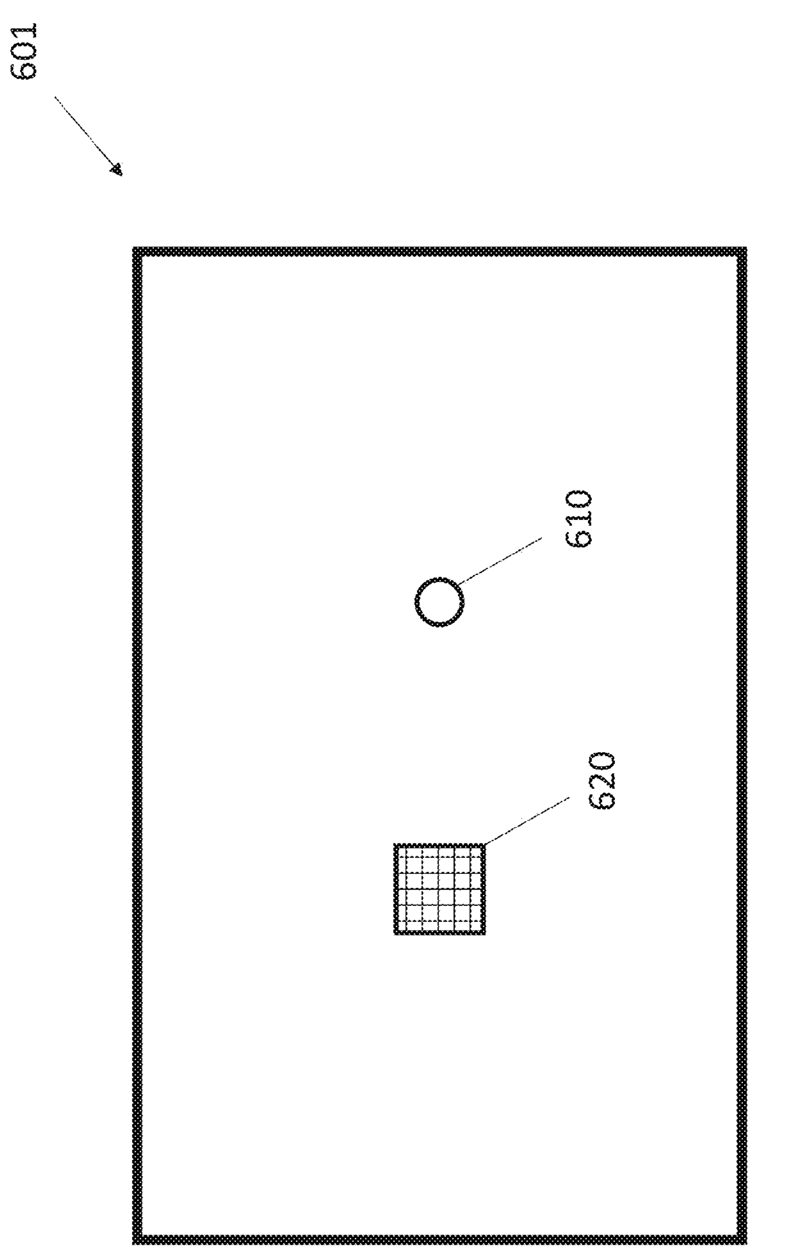
FIG. 21 shows a schematic diagram of an optical sensor module according to some embodiments.

FIG. 21 shows a schematic diagram of an optical sensor module 601 according to some embodiments. Some features of the optical sensor module 601 may be similar to, or the same as, features of other optical sensor modules described herein, including, without limitation, the optical sensor module 501. Therefore, redundant descriptions may be omitted herein.

The optical sensor module 601 may include a light source 610 and an image sensor 620 (e.g., a CMOS image sensor), at least one processing circuit configured to control operations of the optical sensor module 601, and a memory storing instructions that, when executed by the at least one processing circuit, cause the at least one processing circuit to control operations of the optical sensor module 601.

The light source 610 may be configured to illuminate tissue and to illuminate the image sensor 620 through the tissue. The light source 610 may have features similar to, or the same as, the light source 510. For example, the light source 610 may include a laser and one or more speckle mitigation elements, and may be configured to provide only coherent light or to selectively provide coherent light and provide incoherent light. In some examples, the light source 610 is the only light source of the optical sensor module 601.

The image sensor 620 may have a light-capturing photosensitive region having an area less than 30 $mm^2$ (e.g., less than 20 $mm^2$, less than 15 $mm^2$, less than 10 $mm^2$, less than 5 $mm^2$, less than 3 $mm^2$, or less than 1 $mm^2$) and an analog-to-digital converter with 16 or fewer bits (e.g., 12 or fewer bits, 10 or fewer bits, 8 or fewer bits, etc.). In some embodiments, the image sensor 620 also is configured to perform in-pixel DC light subtraction. An image sensor that has a small photosensitive region (e.g., an area less than 30 $mm^2$, 20 $mm^2$, less than 15 $mm^2$, less than 10 $mm^2$, less than 5 $mm^2$, less than 3 $mm^2$, or less than 1 $mm^2$) and has an analog-to-digital converter having a low resolution (e.g., a low number of bits such as 16 or fewer bits, 12 or fewer bits, 10 or fewer bits, or 8 or fewer bits) can be smaller and less expensive than a more complex camera or sensor that has an analog-to-digital converter with a relatively high resolution (e.g., a relatively high number of bits). Such an image sensor can thus be more easily incorporated into a wearable device. In contrast, a more complex and expensive camera or sensor may have a higher resolution (e.g., 24 bits) that is sufficient to enable the camera or sensor to perform digital subtraction of DC light after converting a captured image to digital form (as opposed to analog subtraction of the DC light in the pixel). However, such cameras and sensors are much larger and, thus, can be less suitable for incorporating into a wearable device (e.g., a wrist-type wearable device).

The image sensor 620 is configured to receive one or more light signals from the light source 610, through the tissue, for generating both SPG and PPG measurements. The image sensor 620 may include features similar to, or the same as, features of other image sensors described herein. For example, the image sensor 620 may be configured to perform in-pixel ambient light subtraction and in-pixel DC light subtraction.

The image sensor 620 may be the only light-capturing component on the sensor module. This may mean that there is only one light-capturing component operably configured to capture light from the tissue on the optical sensor module 601 or on a wearable device that the optical sensor module 601 is on. In some embodiments, this may mean that there are no other light-capturing components operably configured to capture light from the tissue within a distance from the light source 610 equal to the product of (i) a distance (e.g., a smallest distance) between the light source 610 and the image sensor 620 and (ii) a set value within a range of 1 to 10 (e.g., 1, 2, 3, 4, or 5). In some embodiments, this may mean that there are no other light-capturing components operably configured to capture light from the tissue within a distance from the image sensor 620 equal to the product of (i) the distance between the light source 610 and the image sensor 620 and (ii) a set value within a range of 0.1 to 10 (e.g., 0.25, 0.5, 0.75, 1, 2, 3, 4, or 5). In some embodiments, the wearable device may include a plurality of optical sensor modules (e.g., a plurality of the optical sensor modules 601), and each of the optical sensor modules includes only one light source (e.g., only the light source 610) and only one light-capturing component (e.g., only the image sensor 620).

By using both a single light source and a single sensor for obtaining both the SPG and PPG measurements, the same tissue may be interrogated for both the SPG and PPG measurements.

Figure 22:
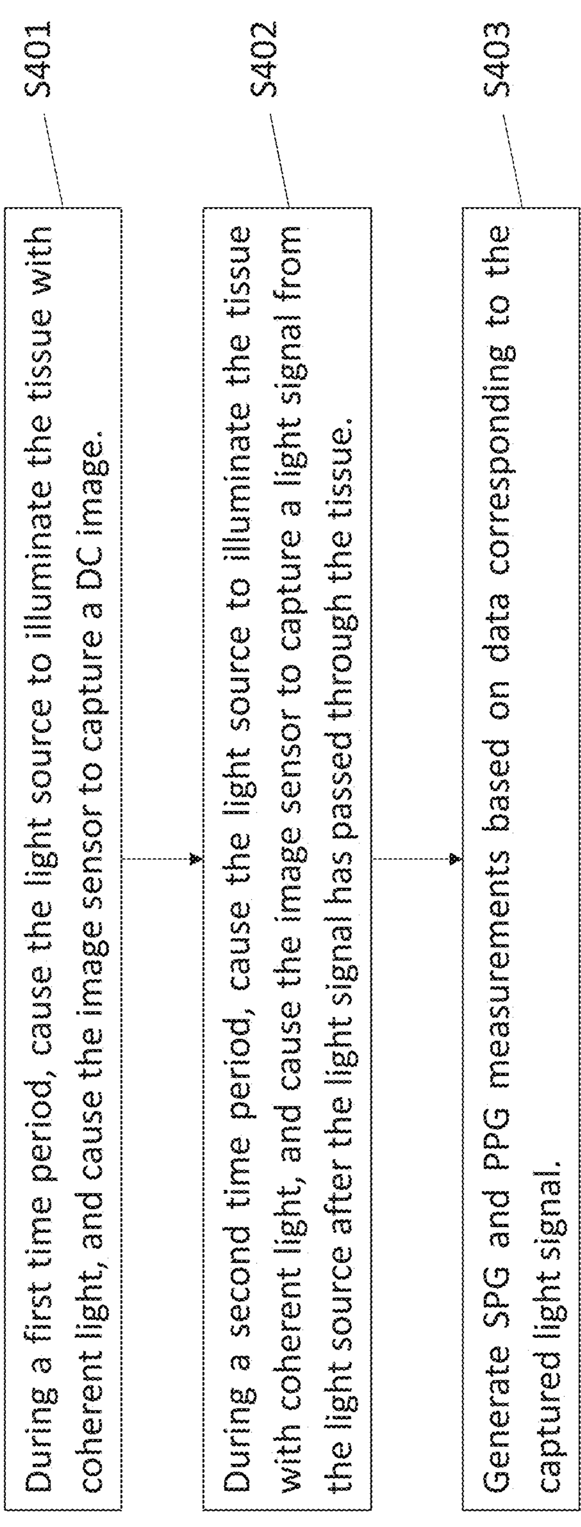
FIGS. 22 and 23 each show operations of the optical sensor module of FIG. 21 according to some embodiments.
Figure 23:
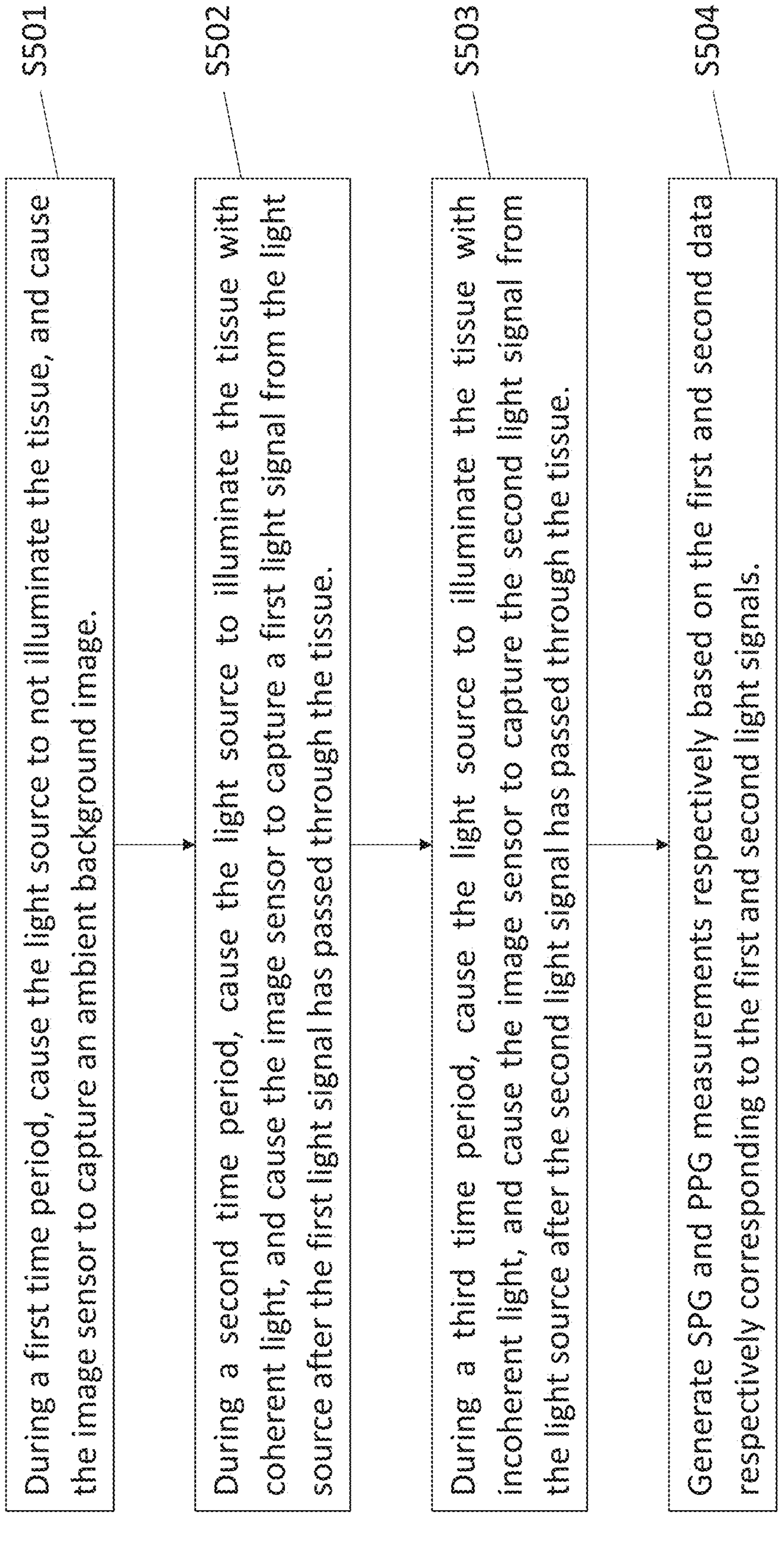

FIGS. 22 and 23 each show operations of the optical sensor module 601 according to some embodiments.

The operations of FIG. 22 may be used, for example, when the light source 610 is configured to provide only coherent light.

In a first operation S401, the at least one processing circuit may be configured to, during a first time period, cause the light source 610 to illuminate the tissue with coherent light, and cause the image sensor 620 to capture a preliminary light signal (e.g., a DC image) reaching the image sensor 620 from the light source 610 through the tissue. During a second operation S402, the at least one processing circuit may be configured to, during a second time period, cause the light source 610 to illuminate the tissue with coherent light, and cause the image sensor 620 to capture a light signal reaching the image sensor 620 from the light source 610 through the tissue. During a third operation S403, the at least one processing circuit may be configured to generate SPG and PPG measurements respectively based on data corresponding to the captured light signal.

For example, the captured DC image may be subtracted out, in-pixel, from the captured light signal, and the resulting image may be digitized to provide the data. In some other embodiments, the DC image and the light signal are separately digitized, and the digitized DC image is digitally subtracted out from the digitized captured light signal before the resulting image is used to generate the SPG and PPG measurements.

In-pixel DC subtraction in an image sensor may be performed in various ways. The image sensor may include an array of pixels, arranged in rows and columns. Each pixel may include a photodiode that, when illuminated, generates a photocurrent. When the pixel is active (e.g., when the photodiode is not shorted), the photodiode may charge a capacitor (which may be referred to as the "storage capacitor" of the pixel, and which may be (i) the capacitance of the photodiode itself or (ii) a separate capacitor). At the end of an exposure, the voltage across the capacitor may be measured, and the capacitor may be discharged (e.g., by shorting its terminals through a reset transistor).

In some embodiments, in-pixel DC subtraction is performed in each pixel by a current source (e.g., a programmable current source) in the pixel which sources or sinks a current (which may be referred to as the "DC current") to discharge the capacitor at a fixed (DC) rate. The DC current may be selected to be equal, or nearly equal, to the expected photocurrent when the pixel is active. In operation, this may cause the capacitor to charge more slowly, and therefore it may cause the pixel to be less likely to saturate.

The DC current of the current source may flow through (and be determined by) a transistor (which may be referred to as a "source transistor") of the current source. The DC current may be programmed by charging a capacitor (which may be referred to as a "DC current control capacitor") which may be connected between ground and the gate of the source transistor. The source transistor may be part of a current mirror, the reference current for which is the current through a reference transistor of the current mirror. The reference transistor may be diode-connected, and a current digital to analog converter (current DAC) may be configured to set the current through the reference transistor. A programming circuit, which is employed to program one or more of the pixels of the image sensor, may include (i) the current DAC (and each pixel may include a respective reference transistor), or (ii) the combination of the current DAC and the reference transistor (and the reference transistor may be shared by a plurality of pixels). In an embodiment in which the reference transistor is part of the programming circuit, the DC current control capacitor may be programmed by temporarily connecting the gate of the reference transistor to the gate of the source transistor.

The programming circuit may program each of a plurality of pixels (e.g., each of the pixels in a row, or each of the pixels in a column, or all of the pixels in the array), one at a time, or all at once. The image sensor may operate (i) in a programming mode, during which each pixel is programmed with a DC current (e.g., by charging the DC current control capacitor of the pixel to a suitable voltage), and (ii) in an operating mode, in which each pixel of the image sensor performs DC subtraction while images are acquired. In the operating mode, the DC current control capacitor (which, as mentioned above, may be connected between the gate of the source transistor and ground) may, having been programmed with a suitable charge, control the current that flows through the source transistor. In the programming mode, the programming circuit (e.g., the current DAC, or the current DAC and the reference transistor) may be temporarily connected (during a programming interval) to the pixel or pixels being programmed (e.g., through suitable control conductors and transistor switches which may select one pixel, or one row, or one column of the image sensor at a time).

For example, the gate of the reference transistor may be connected to the gate of the respective source transistor of one pixel at a time. When such a connection is made, the DC current control capacitor may charge to a voltage that causes the reference current to flow through the source transistor.

As such, in such a system each pixel may be programmed with a different reference current by setting the current DAC to the respective desired DC current as each pixel is programmed. In some embodiments, a plurality of programming circuits (e.g., one programming circuit for each row of the imaging sensor or one programming circuit for each column of the imaging sensor) is employed.

For example, in some embodiments in which the reference transistor is part of the programming circuit and shared by a plurality of pixels, the gate of the reference transistor may be connected, concurrently and temporarily, during a programming interval, to the gates of the source transistors of each of a set of pixels (e.g., each of the pixels of a row or of a column of the imaging detector, or of all of the pixels in the array); in such an embodiment the DC currents of all of the transistors of the set of pixels may be the same. If the set of pixels does not include all of the pixels of the imaging sensor, additional sets of pixels may similarly be programmed, e.g., (i) subsequently by the programming circuit or (ii) concurrently, by other programming circuits. In other embodiments, the pixels are programmed individually, e.g., (i) by a single shared programming circuit or (ii) by a plurality of programming circuits, each being used to program a subset of the pixels.

In some embodiments, each pixel includes a dedicated current DAC and the DC current control capacitor and the components of the current mirror may be unnecessary, e.g., the current DAC may discharge the storage capacitor directly. In such an embodiment, programming may involve programming the current DAC with a suitable digital value (which may be fed to the current DAC as a serial signal; in such an embodiment the current DACs may be serial current DACs, daisy-chained together).

In some embodiments, a calibration exposure is used to program the DC current control capacitor in each pixel acting as an analog memory. A suitable signal on a control conductor connected to each pixel may be used to cause each pixel to operate in programming mode, and the image sensor may then be exposed to light comparable to that expected during operation. During this calibration exposure, the pixel circuit may be configured (e.g., using a current mirror in the pixel circuit, or by temporarily connecting the drain of the source transistor to the gate of the source transistor, so that it is temporarily diode-connected) to cause the charge on the DC current control capacitor to be one that causes, in operating mode, a current approximately equal to the photocurrent during the calibration exposure to flow through the source transistor.

In some embodiments, instead of each pixel including a DC current control capacitor, a control conductor (e.g., a shared control conductor, which may be shared by each of the pixels in a row, or by each of the pixels in a column) may be connected to the gate of the source transistor of each pixel.

The operations of FIG. 23 may be used, for example, when the light source is configured to selectively provide coherent and incoherent light. Some features of the operations of FIG. 23 may be similar to features of the operations of FIG. 22. Therefore, redundant descriptions may be omitted.

During a first operation S501, the at least one processing circuit may be configured to, during a first time period, cause the light source 610 to not illuminate the tissue, and to cause the image sensor 620 to capture an ambient background image. During a second operation S502, the at least one processing circuit may be configured to, during a second time period, cause the light source 610 to illuminate the tissue with coherent light, and cause the image sensor 620 to capture the first light signal reaching the image sensor 620 from the light source 610 through the tissue. During a third operation S503, the at least one processing circuit may be configured to, during a third time period, cause the light source 610 to illuminate the tissue with incoherent light, and to cause the image sensor 620 to capture the second light signal reaching the image sensor 620 from the light source 610 through the tissue. During a fourth operation S504, the at least one processing circuit may be configured to generate SPG and PPG measurements respectively based on first and second data corresponding to the first and second light signals.

In some examples, an optical sensor module described herein may include one set of light source(s) and a plurality of sets of optical detector(s).

For example, the optical sensor module 501 may include a single light source (e.g., the light source 510) and a plurality of pairs (e.g., 2, 3, 4, 5, or more pairs) of an image sensor and a photodiode, and the single light source may be configured to illuminate, through the tissue, each image sensor and each photodiode in each of the plurality of pairs. A distance between the image sensor and the photodiode in each of the plurality of pairs may be any distance that the third distance 501D3 can be. Each image sensor in the plurality of pairs may be configured with any features that the image sensor 520 may be configured to have, and each photodiode in the plurality of pairs may be configured with any features that the photodiode 530 may have. The plurality of pairs may be arranged around the single light source. Embodiments including the single light source and the plurality of pairs may improve the case in placing the optical sensor module 501 on a user.

In some examples, the optical sensor module 601 may include a single light source (e.g., the light source 610) and a plurality (e.g., 2, 3, 4, 5, or more) of image sensors, and the single light source may be configured to illuminate, through the tissue, each of the plurality of image sensors. The plurality of image sensors may be arranged around the single light source. Each image sensor in the plurality of image sensors may be configured with any features that the image sensor 620 may be configured to have.

Each of the terms "processing circuit" and "means for processing" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general-purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example, a processing circuit may include two processing circuits, an FPGA and a CPU, interconnected on a PCB.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., (1−35/100) times 10) and the recited maximum value of 13.5 (i.e., (1+35/100) times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

While the invention has been described in conjunction with the exemplary embodiments described above, many equivalent modifications and variations will be apparent to those skilled in the art when given this disclosure. For example, features described in one embodiment and consistent with another embodiment disclosed herein may be used in the other embodiment, unless the present disclosure indicates otherwise, and all such embodiments and encompassed within the present disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A wearable device, comprising a first optical sensor module, the first optical sensor module comprising:
- an image sensor configured to receive light from biological tissue;
- a photodiode configured to receive light from the tissue;
- a light source comprising a laser and being configured to illuminate, through the tissue, each of the image sensor and the photodiode, a distance between the image sensor and the photodiode being less than 50% of the distance between the image sensor and the light source; and
- at least one processing circuit configured to process first data corresponding to a first light signal received by the image sensor from the light source to generate a speckleplethysmography (SPG) measurement, and to process second data corresponding to a second light signal received by the photodiode from the light source to generate a photoplethysmography (PPG) measurement.

2. The wearable device of claim 1, wherein the light source is configured to illuminate the tissue with only coherent light.

3. The wearable device of claim 1, wherein the light source is the only light source in the first optical sensor module.

4. The wearable device of claim 1, wherein the image sensor and the photodiode are each spaced apart from the laser by a substantially same distance.

5. The wearable device of claim 1, wherein one of the image sensor and the photodiode is positioned between the laser and the other one of the image sensor and the photodiode.

6. The wearable device of claim 1, wherein the at least one processing circuit is configured to cause the image sensor and the photodiode to concurrently capture the first light signal and the second light signal, respectively.

7. The wearable device of claim 1, wherein:
- the light source is configured to selectively illuminate the tissue with coherent light or incoherent light;
- the at least one processing circuit is configured to:
  - during a first time period, cause the light source to illuminate the tissue with coherent light, and to cause the image sensor to capture the first light signal from the light source; and
  - during a second time period, cause the light source to illuminate the tissue with incoherent light, and to cause the photodiode to capture the second light signal from the light source.

8. The wearable device of claim 7, wherein the light source is configured to selectively generate the incoherent light by selectively applying one or more speckle mitigation techniques to coherent light generated by the laser.

9. The wearable device of claim 7, wherein the laser is selectively operable in a first state, wherein light generated by the laser is coherent, and in a second state, wherein light generated by the laser is incoherent.

10. The wearable device of claim 1, wherein the image sensor is a first image sensor and the photodiode is a first photodiode, and
- wherein the first optical sensor further comprises a second image sensor and a second photodiode, the light source being configured to illuminate, through the tissue, each of the second image sensor and the second photodiode, and a distance between the second image sensor and the second photodiode being less than 50% of the distance between the first image sensor and the light source.

11. The wearable device of claim 1, wherein the photodiode is configured to perform at least one of in-pixel ambient light subtraction or in-pixel DC light subtraction.

12. A wearable device, comprising a first optical sensor module, the first optical sensor module comprising:
- an image sensor configured to receive light from biological tissue;
- a light source comprising a laser and being configured to illuminate, through the tissue, the image sensor; and
- at least one processing circuit configured to process first data corresponding to a first light signal received by the image sensor from the light source to generate a speckleplethysmography (SPG) measurement, and to process second data corresponding to a second light signal received by the image sensor from the light source to generate a photoplethysmography (PPG) measurement,
- wherein the image sensor is configured to perform in-pixel DC light subtraction.

13. The wearable device of claim 12, wherein a photosensitive surface of the image sensor configured to capture light has an area of less than 5 $mm^2$ and an analog to digital converter with 12 or fewer bits.

14. The wearable device of claim 12, wherein:
- the light source is configured to selectively illuminate the tissue with coherent light and incoherent light; and
- the at least one processing circuit is configured to:
  - during a first time period, cause the light source to illuminate the tissue with coherent light, and to cause the image sensor to capture the first light signal from the light source; and
  - during a second time period, cause the light source to illuminate the tissue with incoherent light, and to cause the image sensor to capture the second light signal from the light source.

15. The wearable device of claim 14, wherein the light source is configured to selectively generate the incoherent light by selectively applying one or more speckle mitigation techniques to coherent light generated by the laser.

16. The wearable device of claim 14, wherein the laser is selectively operable in a first state, wherein light generated by the laser is coherent, and in a second state, wherein light generated by the laser is incoherent.

17. The wearable device of claim 12, wherein the second light signal is the same as the first light signal, and wherein the at least one processing circuit is configured to, during a first time period, cause the light source to illuminate the tissue with only coherent light, and cause the image sensor to capture the first light signal from the tissue, and wherein the at least one processing circuit is configured to generate both the SPG measurement and the PPG measurement based on data corresponding to the first light signal.

18. The wearable device of claim 12, wherein the light source is the only light source in the optical sensor module, and the image sensor is the only light-capturing component in the optical sensor module.

19. A wearable device, comprising a first optical sensor module, the first optical sensor module comprising:

an image sensor configured to receive light from biological tissue;

a light source comprising a laser, the light source being configured to selectively generate coherent and incoherent light and to illuminate, through the tissue, the image sensor; and at least one processing circuit configured to process first data corresponding to a first light signal received by the image sensor from the light source to generate a speckleplethysmography (SPG) measurement, and to process second data corresponding to a second light signal received by the image sensor from the light source to generate a photoplethysmography (PPG) measurement.

20. The wearable device of claim 19, wherein the light source is configured to selectively generate the coherent and incoherent light by selectively applying one or more speckle mitigation techniques to light generated by the laser.

* * * * *